(12) United States Patent
Hellingwerf et al.

(10) Patent No.: US 10,273,490 B2
(45) Date of Patent: Apr. 30, 2019

(54) ERYTHRITOL PRODUCTION IN CYANOBACTERIA

(71) Applicant: Photanol B.V., Amsterdam (NL)

(72) Inventors: Klaas Jan Hellingwerf, Amsterdam (NL); Vinod Puthan Veetil, Amsterdam (NL); Aniek Doreen van der Woude, Amsterdam (NL)

(73) Assignee: PHOTANOL B.V., Amsterdam (NL)

( * ) Notice: Subject to any disclaimer, the term of this patent is extended or adjusted under 35 U.S.C. 154(b) by 0 days.

(21) Appl. No.: 15/129,459

(22) PCT Filed: Mar. 27, 2015

(86) PCT No.: PCT/NL2015/050195
§ 371 (c)(1),
(2) Date: Sep. 27, 2016

(87) PCT Pub. No.: WO2015/147644
PCT Pub. Date: Oct. 1, 2015

(65) Prior Publication Data
US 2017/0114349 A1 Apr. 27, 2017

(30) Foreign Application Priority Data
Mar. 27, 2014 (EP) .................................... 14161951

(51) Int. Cl.
*C12N 15/52* (2006.01)
*C12N 15/74* (2006.01)
*C12P 7/18* (2006.01)
*C12N 9/02* (2006.01)
*C12N 9/16* (2006.01)

(52) U.S. Cl.
CPC ........... *C12N 15/74* (2013.01); *C12N 9/0008* (2013.01); *C12N 9/16* (2013.01); *C12N 15/52* (2013.01); *C12P 7/18* (2013.01); *C12Y 102/01072* (2013.01); *C12Y 301/03* (2013.01)

(58) Field of Classification Search
CPC .......... C12N 15/74; C12N 15/52; C12N 9/16; C12N 9/0008; C12Y 301/03; C12Y 102/01072; C12P 7/18
See application file for complete search history.

(56) References Cited

U.S. PATENT DOCUMENTS

2002/0160480 A1 10/2002 Ookura et al.
2011/0300597 A1 12/2011 Burk et al.

FOREIGN PATENT DOCUMENTS

EP 2436772 A1 4/2012
WO 2013/130394 A1 9/2013

OTHER PUBLICATIONS

Ding et al., Gen Bank accession No. AL169479, Nov. 24, 2015.*
Ding et al., Gen Bank accession No. CP012832, Nov. 24, 2015.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al. Current Opinion in Structural Biology 19:357-362, 2009.*
Fuszard et al., "The quantitative proteomic response of *Synechocystis* sp. PCC6803 to phosphate acclimation"; Aquatic Biosystems; Biomed Central Ltd., vol. 9, No. 1, (Feb. 26, 2013), pp. 5.
Park et al., "Proteomics and physiology of erythritol-producing stains"; Journal of Chromatography B; Biomedical Sciences & Applications, Elsevier; vol. 815, No. 1-2, (Feb. 5, 2005), pp. 251-260.
Moon et al., "Biotechnological production of erythritol and its applications"; Applied Microbiology Biotechnology; Springer, vol. 86, No. 4, (Feb. 26, 2010), pp. 1017-1025.
International Search Report and Written Opinion for PCT/NL2015/050195.

* cited by examiner

*Primary Examiner* — Delia M Ramirez
(74) *Attorney, Agent, or Firm* — Volpe and Koenig, P.C.

(57) ABSTRACT

The present invention relates to a process for producing erythritol and to a cyanobacterial cell for the production of erythritol.

Figure 1:
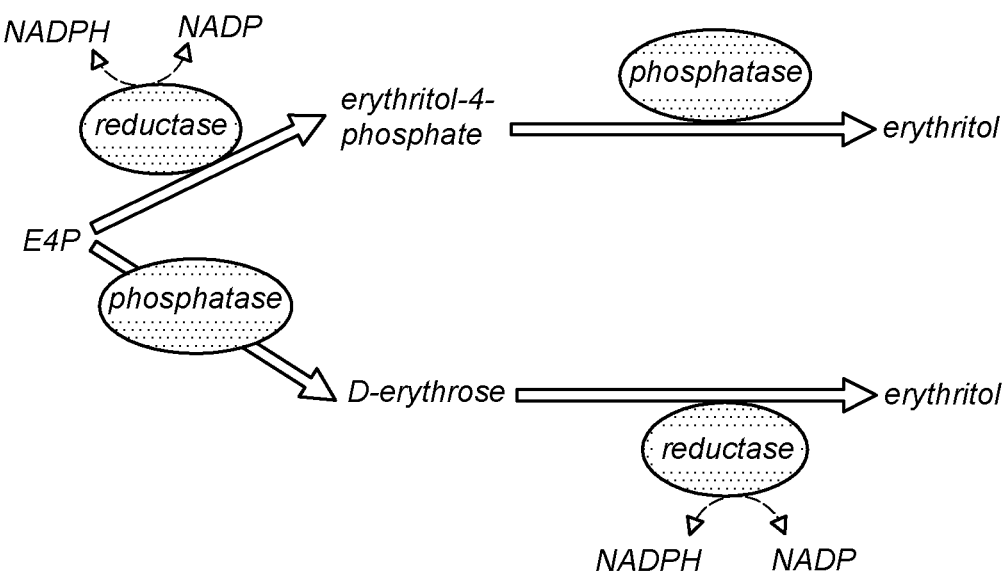

9 Claims, 4 Drawing Sheets
Specification includes a Sequence Listing.

SEQUENCE LISTING

```
<160> NUMBER OF SEQ ID NOS: 16

<210> SEQ ID NO 1
<211> LENGTH: 813
<212> TYPE: DNA
<213> ORGANISM: Escherichia coli

<400> SEQUENCE: 1
atggctatta aactcattgc tatcgatatg gatggcaccc ttctgctgcc cgatcacacc      60
atttcacccg ccgttaaaaa tgcgattgcc gcagctcgcg cccgtggcgt gaatgtcgtg     120
ctaacgacgg gtcgcccgta tgcaggtgtg cacaactacc tgaaagagct gcatatggaa     180
cagccgggcg actactgcat tacttataac ggcgcgctgg tacagaaggc cgctgatggt     240
agcaccgtgg cgcaaactgc tctcagctat gacgactatc gtttcctgga aaaactctct     300
cgcgaagtcg gttctcattt ccacgccctg gaccgcacca cgctgtacac cgccaaccgt     360
gatatcagct actacacggt gcatgaatcc ttcgttgcca ccattccgct ggtgttctgc     420
```

-continued

```
gaagcggaga aaatggaccc caatacccag ttcctgaaag tgatgatgat tgatgaaccc    480
gccatcctcg accaggctat cgcgcgtatt ccgcaggaag tgaaagagaa atataccgtg    540
ctgaaaagtg cgccgtactt cctcgaaatc ctcgataaac gcgttaacaa aggtacgggg    600
gtgaaatcac tggccgacgt gttaggtatt aaaccggaag aaatcatggc gattggcgat    660
caggaaaacg atatcgcaat gattgaatat gcaggcgtcg gtgtggcgat ggataacgct    720
attccttcag tgaaagaagt ggcgaacttt gtcaccaaat ctaaccttga agatggcgtg    780
gcgtttgcta ttgagaagta tgtgctgaat taa                                 813
```

<210> SEQ ID NO 2
<211> LENGTH: 270
<212> TYPE: PRT
<213> ORGANISM: Escherichia coli
<400> SEQUENCE: 2

```
Met Ala Ile Lys Leu Ile Ala Ile Asp Met Asp Gly Thr Leu Leu
1               5                   10                  15

Pro Asp His Thr Ile Ser Pro Ala Val Lys Asn Ala Ile Ala Ala
                20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270
```

<210> SEQ ID NO 3
<211> LENGTH: 840
<212> TYPE: DNA
<213> ORGANISM: Synechocystis PCC6803

<400> SEQUENCE: 3

```
gtgtcaatca agttagtagt attggacatt gatggcacca tcgccggagt atccaatcaa    60
attaacccgt cagtggtgaa aaccattcac caggtacaga gccggggtat ccaagtggcg   120
ttggccactg gccgtatgtt tagttctgct ctacggttcc atcagaccat tcaatcaacc   180
ctgcctttga ttagttacaa cggtgcccta accaagcatc cccacactgg tgctgtttta   240
agggaaaaac ccctgccccc ggcgatcgcc ttggaaattt tggaccattt tgagcgaccg   300
gaactggaac ccatcttga tatccactgc tattacaacg accagctcca tgtgcggcat   360
atcaccccag aaacccatgt ttatatggaa aggtccggtg ccatggccca agctagcggc   420
gatctacgct caattattga attgggtagc accaccaaaa tgttagccat cagtcgcaat   480
gctcccctca tggcccagtt gatggcgaaa atgggtcaaa aactccaggg ccaagccgtg   540
catctgaccc aatccaccga gatttacttt gaagtcaccc acgccgaagc caccaaaggc   600
ctggccctgc aacatttagc tgaagacgtg ttagggcttg atccccaaga agttttggcg   660
atcggagaca attttaacga cgtggaaatg ctgaaatatg ccggagtggg ggtagccatg   720
ggtaatgctc ccccggaagt gcaaaaggtg gcagactggg taacggcgga cgtggaagcc   780
gatggagtgt cccaagcctt ggctaggttc tgcctagatt caaccctagc actctgttaa   840
```

<210> SEQ ID NO 4
<211> LENGTH: 279
<212> TYPE: PRT
<213> ORGANISM: Synechocystis PCC6803

<400> SEQUENCE: 4

```
Met Ser Ile Lys Leu Val Val Leu Asp Ile Asp Gly Thr Ile Ala Gly
1               5                   10                  15

Val Ser Asn Gln Ile Asn Pro Ser Val Val Lys Thr Ile His Gln Val
            20                  25                  30

Gln Ser Arg Gly Ile Gln Val Ala Leu Ala Thr Gly Arg Met Phe Ser
        35                  40                  45

Ser Ala Leu Arg Phe His Gln Thr Ile Gln Ser Thr Leu Pro Leu Ile
    50                  55                  60

Ser Tyr Asn Gly Ala Leu Thr Lys His Pro His Thr Gly Ala Val Leu
65                  70                  75                  80

Arg Glu Lys Pro Leu Pro Pro Ala Ile Ala Leu Glu Ile Leu Asp His
                85                  90                  95

Phe Glu Arg Pro Glu Leu Glu Pro His Leu Asp Ile His Cys Tyr Tyr
            100                 105                 110

Asn Asp Gln Leu His Val Arg His Ile Thr Pro Glu Thr His Val Tyr
        115                 120                 125

Met Glu Arg Ser Gly Ala Met Ala Gln Ala Ser Gly Asp Leu Arg Ser
    130                 135                 140

Ile Ile Glu Leu Gly Ser Thr Thr Lys Met Leu Ala Ile Ser Arg Asn
145                 150                 155                 160

Ala Pro Leu Met Ala Gln Leu Met Ala Glu Met Gly Gln Lys Leu Gln
                165                 170                 175

Gly Gln Ala Val His Leu Thr Gln Ser Thr Glu Ile Tyr Phe Glu Val
            180                 185                 190

Thr His Ala Glu Ala Thr Lys Gly Leu Ala Leu Gln His Leu Ala Glu
        195                 200                 205

Asp Val Leu Gly Leu Asp Pro Gln Glu Val Leu Ala Ile Gly Asp Asn
    210                 215                 220
```

```
Phe Asn Asp Val Glu Met Leu Lys Tyr Ala Gly Val Gly Val Ala Met
225                 230                 235                 240

Gly Asn Ala Pro Pro Glu Val Gln Lys Val Ala Asp Trp Val Thr Ala
            245                 250                 255

Asp Val Glu Ala Asp Gly Val Ser Gln Ala Leu Ala Arg Phe Cys Leu
        260                 265                 270

Asp Ser Thr Leu Ala Leu Cys
        275

<210> SEQ ID NO 5
<211> LENGTH: 651
<212> TYPE: DNA
<213> ORGANISM: Thermotoga maritima

<400> SEQUENCE: 5
atggaagcgg tgattttcga catggatgga gtgctcatgg acacagagcc tctctacttc      60
gaagcttaca gaagagtcgc ggaaagctat ggaaaacctt acacggagga tctccacagg     120
agaataatgg gagttcctga agagaaggt cttcccatcc tcatggaagc tctggagata     180
aaagattctc tggagaactt caaaaagagg gtccacgaag aaaaaaagcg cgttttctct     240
gagcttctca aggaaaatcc gggtgtaaga gaggcgctcg agttcgtaaa gagcaaaaga     300
ataaaactcg cgctcgcaac ctccacacca cagcgagaag cgctggagag attgagaaga     360
ctcgatctcg aaaagtactt cgacgtcatg gtgttcggtg atcaggtgaa gaacggaaag     420
cctgatccag agatatacct tctcgttctg gaaaggttga atgtggtccc agagaaggtt     480
gtggtcttcg aagactcaaa gagcggtgtt gaagccgcaa aaagcgccgg catagaaaga     540
atctatggag tcgttcactc tttgaacgac ggtaaagcgc ttcttgaagc gggtgcggtt     600
gctctggtga acccgagga atcctgaac gttctcaaag aggttcttta a                651

<210> SEQ ID NO 6
<211> LENGTH: 216
<212> TYPE: PRT
<213> ORGANISM: Thermotoga maritima

<400> SEQUENCE: 6

Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Pro Glu Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
```

```
                145                 150                 155                 160
Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
        210                 215

<210> SEQ ID NO 7
<211> LENGTH: 939
<212> TYPE: DNA
<213> ORGANISM: Saccharomyces cerevisiae

<400> SEQUENCE: 7
atgcctgcta ctttacatga ttctacgaaa atcctttctc taaatactgg agcccaaatc      60
cctcaaatag gtttaggtac gtggcagtcg aaagagaacg atgcttataa ggctgtttta     120
accgctttga agatggcta ccgacacatt gatactgctg ctatttaccg taatgaagac      180
caagtcggtc aagccatcaa ggattcaggt gttcctcggg aagaaatctt tgttactaca    240
aagttatggt gtacacaaca ccacgaacct gaagtagcgc tggatcaatc actaaagagg    300
ttaggattgg actacgtaga cttatatttg atgcattggc ctgccagatt agatccagcc    360
tacatcaaaa atgaagacat cttgagtgtg ccaacaaaga aggatggttc tcgtgcagtg    420
gatatcacca attggaattt catcaaaacc tgggaattaa tgcaggaact accaaagact    480
ggtaaaacta aggccgttgg agtctccaac ttttctataa ataacctgaa agatctatta    540
gcatctcaag gtaataagct tacgccagct gctaaccaag tcgaaataca tccattacta    600
cctcaagacg aattgattaa ttttgtaaaa gtaaaggca ttgtggttga agcttattct     660
ccgttaggta gtaccgatgc tccactattg aaggaaccgg ttatccttga aattgcgaag    720
aaaaataacg ttcaacccgg acacgttgtt attagctggc acgtccaaag aggttatgtt    780
gtcttgccaa atctgtgaa tcccgatcga atcaaaacga acaggaaaat atttactttg    840
tctactgagg actttgaagc tatcaataac atatcgaagg aaaagggcga aaaagggtt    900
gtacatccaa attggtctcc tttcgaagta ttcaagtaa                           939

<210> SEQ ID NO 8
<211> LENGTH: 312
<212> TYPE: PRT
<213> ORGANISM: Saccharomyces cerevisiae

<400> SEQUENCE: 8

Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
            20                  25                  30

Asn Asp Ala Tyr Lys Ala Val Leu Thr Ala Leu Lys Asp Gly Tyr Arg
        35                  40                  45

His Ile Asp Thr Ala Ala Ile Tyr Arg Asn Glu Asp Gln Val Gly Gln
    50                  55                  60

Ala Ile Lys Asp Ser Gly Val Pro Arg Glu Glu Ile Phe Val Thr Thr
65                  70                  75                  80

Lys Leu Trp Cys Thr Gln His His Glu Pro Glu Val Ala Leu Asp Gln
                85                  90                  95
```

```
Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
        115                 120                 125

Ser Val Pro Thr Lys Lys Asp Gly Ser Arg Ala Val Asp Ile Thr Asn
    130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255

Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
        275                 280                 285

Asn Asn Ile Ser Lys Glu Lys Gly Glu Lys Arg Val Val His Pro Asn
    290                 295                 300

Trp Ser Pro Phe Glu Val Phe Lys
305                 310

<210> SEQ ID NO 9
<211> LENGTH: 849
<212> TYPE: DNA
<213> ORGANISM: Candida magnoliae

<400> SEQUENCE: 9
atgtcttcga cctacaccct tactcgcctg tctgcgcctt caatggtgct caacagtggc      60
tcccagatcc ctgccgttgg ctatggactc tggaaacagc agggcagcga ggccaaggac     120
tccgtgcgct gcgccatcga gtctggctac cgtcaccttg actgtgcaac cgcttaccag     180
aaccacaaag aggtcggcca agctattcgt gaggccggcg tgcctcgcga cgaactgtgg     240
atcacgtcca aggtttgggg cacgcacttc gacaaccctg aagagggact tgacgacatt     300
ctcgaggagc tcggtgtcga ataccctgga ctgctactcc tccacctgcc agtcgcgttc     360
aagcggaacc cggaggaccc gaagcagctg cgcggccttc ctgtggacca cgacatgaag     420
tacgccgacg tgtgggcgcg catggagaag ctgcccaagt cgaaggtgcg gaacattggt     480
gtgtcgaacc tcacggtgag ggcgctggat gagcttttgc agacggcgaa ggtgactccg     540
gccgtgaacc aggtcgagat gcacccgaac ctgcctcaga gaagctgctc gactactgc      600
aagtcgaagg gcattgttgt gcaggcatac agccctctgg ctcagggcca gcacgagaac     660
ccagttgtca cagacatcgc cgacgacctc ggcgtctcgc cggcgcaagt cgtgctttcg     720
tggggcgcct tgcgcggcac gaacattctt cccaaatcct cgacgccctc cgtgtattcgc    780
gagaacctcg aactcatcca gcttagcgac gaccacatga ggcgtattga cgcgctagca     840
``` agacggtga                                                          849

<210> SEQ ID NO 10
<211> LENGTH: 282
<212> TYPE: PRT
<213> ORGANISM: Candida magnoliae

<400> SEQUENCE: 10

Met Ser Ser Thr Tyr Thr Leu Thr Arg Leu Ser Ala Pro Ser Met Val
1               5                   10                  15

Leu Asn Ser Gly Ser Gln Ile Pro Ala Val Gly Tyr Gly Leu Trp Lys
            20                  25                  30

Gln Gln Gly Ser Glu Ala Lys Asp Ser Val Arg Cys Ala Ile Glu Ser
        35                  40                  45

Gly Tyr Arg His Leu Asp Cys Ala Thr Ala Tyr Gln Asn His Lys Glu
    50                  55                  60

Val Gly Gln Ala Ile Arg Glu Ala Gly Val Pro Arg Asp Glu Leu Trp
65                  70                  75                  80

Ile Thr Ser Lys Val Trp Gly Thr His Phe Asp Asn Pro Glu Glu Gly
                85                  90                  95

Leu Asp Asp Ile Leu Glu Glu Leu Gly Val Glu Tyr Leu Asp Leu Leu
            100                 105                 110

Leu Leu His Leu Pro Val Ala Phe Lys Arg Asn Pro Glu Asp Pro Lys
        115                 120                 125

Gln Leu Arg Gly Leu Pro Val Asp His Asp Met Lys Tyr Ala Asp Val
    130                 135                 140

Trp Ala Arg Met Glu Lys Leu Pro Lys Ser Lys Val Arg Asn Ile Gly
145                 150                 155                 160

Val Ser Asn Leu Thr Val Arg Ala Leu Asp Glu Leu Leu Gln Thr Ala
                165                 170                 175

Lys Val Thr Pro Ala Val Asn Gln Val Glu Met His Pro Asn Leu Pro
            180                 185                 190

Gln Lys Lys Leu Leu Asp Tyr Cys Lys Ser Lys Gly Ile Val Val Gln
        195                 200                 205

Ala Tyr Ser Pro Leu Ala Gln Gly Gln His Glu Asn Pro Val Val Thr
    210                 215                 220

Asp Ile Ala Asp Leu Gly Val Ser Pro Ala Gln Val Val Leu Ser
225                 230                 235                 240

Trp Gly Ala Leu Arg Gly Thr Asn Ile Leu Pro Lys Ser Ser Thr Pro
                245                 250                 255

Ser Arg Ile Arg Glu Asn Leu Glu Leu Ile Gln Leu Ser Asp Asp His
            260                 265                 270

Met Arg Arg Ile Asp Ala Leu Ala Arg Arg
        275                 280

<210> SEQ ID NO 11
<211> LENGTH: 996
<212> TYPE: DNA
<213> ORGANISM: Hypocrea jecorina

<400> SEQUENCE: 11
atgtcttccg aaggaccgt caccctcaac accggctaca agatccccca gatcggctac    60
ggcacctggc aggccgctcc cggcgaggtc ggcgctggtg tctttgaggc cctcaaggtt   120
ggctaccgcc acctcgacct ggccaaggtc tacggcaacc agaaggaggt tggtgagggc   180
atcaagaagg ctcttgctga ggtccccggc ctgaagcgcg aggatatttt catcacctcc   240

```
aagctgtgga acaactccca caagcccgag gacgtcgagc ccgctctcga cgacaccctg    300
gccgagcttg gcctcgacta ccttgacctc tacctcatcc actggcccgt tgcctttgct    360
cccggcgccg acctcttccc caagtccgag gacggctccg aggtgcagct caaccagaat    420
gtgtccattg tccagacctg gaaggccatg accgagctgc ccaagtccaa ggtccgctcc    480
gtcggtgtct ccaactttac cattgagcac ctcgacgccg tcatcgaggc caccggcgtc    540
gtccccgccg tcaaccagat cgagcgccac ccccgcctcc caaccagcc cctgatcgac    600 tactgcgcca agaagggcat catcatcacc gcctactccg cctttggcaa caacacaaag    660
ggcctgcccc tgctcgtcag ctccgacgag gtcaaggccg tcgccgacaa cctgtccaag    720
aagcagggca agaccgtcac tcccgcccag gtcatcctcg cctggtccca gattggtggc    780
cacaccgtca ttcccaagtc cgtcaccaag gcgcgcattg cggagaactt ccaggaggtt    840
gagctggatg acgaggccat tgctgcgctg aacaagttgg gcgagaagcc tcagcggttc    900
aacattcctt acacctacaa gcctaggtgg aacattaacc tgttcaacac cgaggaggag    960
aaggccgctg cccacactgc tgtcatcaag ctgtaa                              996
```

<210> SEQ ID NO 12  
<211> LENGTH: 331  
<212> TYPE: PRT  
<213> ORGANISM: Hypocrea jecorina

<400> SEQUENCE: 12

```
Met Ser Ser Gly Arg Thr Val Thr Leu Asn Thr Gly Tyr Lys Ile Pro
1               5                   10                  15

Gln Ile Gly Tyr Gly Thr Trp Gln Ala Ala Pro Gly Glu Val Gly Ala
            20                  25                  30

Gly Val Phe Glu Ala Leu Lys Val Gly Tyr Arg His Leu Asp Leu Ala
        35                  40                  45

Lys Val Tyr Gly Asn Gln Lys Glu Val Gly Glu Gly Ile Lys Lys Ala
    50                  55                  60

Leu Ala Glu Val Pro Gly Leu Lys Arg Glu Asp Ile Phe Ile Thr Ser
65                  70                  75                  80

Lys Leu Trp Asn Asn Ser His Lys Pro Glu Asp Val Glu Pro Ala Leu
                85                  90                  95

Asp Asp Thr Leu Ala Glu Leu Gly Leu Asp Tyr Leu Asp Leu Tyr Leu
            100                 105                 110

Ile His Trp Pro Val Ala Phe Ala Pro Gly Ala Asp Leu Phe Pro Lys
        115                 120                 125

Ser Glu Asp Gly Ser Glu Val Gln Leu Asn Gln Asn Val Ser Ile Val
    130                 135                 140

Gln Thr Trp Lys Ala Met Thr Glu Leu Pro Lys Ser Lys Val Arg Ser
145                 150                 155                 160

Val Gly Val Ser Asn Phe Thr Ile Glu His Leu Asp Ala Val Ile Glu
                165                 170                 175

Ala Thr Gly Val Val Pro Ala Val Asn Gln Ile Glu Arg His Pro Arg
            180                 185                 190

Leu Pro Asn Gln Pro Leu Ile Asp Tyr Cys Ala Lys Lys Gly Ile Ile
        195                 200                 205

Ile Thr Ala Tyr Ser Ala Phe Gly Asn Asn Thr Lys Gly Leu Pro Leu
    210                 215                 220

Leu Val Ser Ser Asp Glu Val Lys Ala Val Ala Asp Asn Leu Ser Lys
225                 230                 235                 240
```

Lys Gln Gly Lys Thr Val Thr Pro Ala Gln Val Ile Leu Ala Trp Ser
                245                 250                 255

Gln Ile Gly Gly His Thr Val Ile Pro Lys Ser Val Thr Lys Ala Arg
            260                 265                 270

Ile Ala Glu Asn Phe Gln Glu Val Glu Leu Asp Asp Glu Ala Ile Ala
        275                 280                 285

Ala Leu Asn Lys Leu Gly Glu Lys Pro Gln Arg Phe Asn Ile Pro Tyr
    290                 295                 300

Thr Tyr Lys Pro Arg Trp Asn Ile Asn Leu Phe Asn Thr Glu Glu Glu
305                 310                 315                 320

Lys Ala Ala Ala His Thr Ala Val Ile Lys Leu
                325                 330

<210> SEQ ID NO 13
<211> LENGTH: 1005
<212> TYPE: DNA
<213> ORGANISM: Aspergillus niger

<400> SEQUENCE: 13
atgtctctcg gaaagaaggt tactctcaac tccggtgctc agatccccca gctgggattt      60
ggtacctggc agtctgcccc cggtcaggtc ggtgatgccg tctacgaggc cttgaaggcc     120
ggctaccgcc acttggatct ggctactatc taccagaacc agcgcgaggt tgctgagggc     180
atcaagagag cctacaagga cgtccctggc ctcaagcgtg aggacatctt catcacctcc     240
aagctgtgga actcccagca cgaccccgcc gttgttgaga aggctctgga tgagtgcctt     300
gctgagctcg agctcgacta cctcgatctc tacctcgtcc actggcccgt ttccttcacc     360
accggctccg agttgttccc cctcgtcaag gacagctccg ttgagggcgg tgatgtcgtg     420
atcaacgacg acatctccat cgtcgacacc tggaaggcca tgacccagct ccccaagagc     480
aaggcccgca ccgtcggtgt ctccaaccac atgatccctc acctcgaggc catcatcaac     540
gccaccggcg ttgtccccgc cgttaaccag atcgagcgcc accccgttct ccagagcaac     600
gagctcatcg aatactgcca agaagagggc atccacgtga ccgcctactc tgccttcggc     660
aacaacggct tcggcgtccc cctcctcgtc acccgccccg aagtcaagga agtcgctgag     720
tccgcctcca gcgcctcgg caccaccgtc acccctgccc aggtcatcct ggcctggtcc     780
caggtcggcg ccacagtgt catccccaag tcggtgacgc cgtcccgcat ccatgagaac     840
ttcaaggagg tggagctcac tcccgaggaa atcgccaagg tgtccgagct gggcaaggac     900
cgcagacgct acaacactcc ttacgttgct aacacgcctc gctgggatat cgacatcttc     960
ggtgaggagg aggagaagcc tgctggtcat aaggtgattg tttaa                    1005

<210> SEQ ID NO 14
<211> LENGTH: 334
<212> TYPE: PRT
<213> ORGANISM: Aspergillus niger

<400> SEQUENCE: 14

Met Ser Leu Gly Lys Lys Val Thr Leu Asn Ser Gly Ala Gln Ile Pro
1               5                   10                  15

Gln Leu Gly Phe Gly Thr Trp Gln Ser Ala Pro Gly Gln Val Gly Asp
            20                  25                  30

Ala Val Tyr Glu Ala Leu Lys Ala Gly Tyr Arg His Leu Asp Leu Ala
        35                  40                  45

Thr Ile Tyr Gln Asn Gln Arg Glu Val Ala Glu Gly Ile Lys Arg Ala

```
            50              55              60
Tyr Lys Asp Val Pro Gly Leu Lys Arg Glu Asp Ile Phe Ile Thr Ser
 65                  70                  75                  80

Lys Leu Trp Asn Ser Gln His Asp Pro Ala Val Val Glu Lys Ala Leu
                 85                  90                  95

Asp Glu Cys Leu Ala Glu Leu Glu Leu Asp Tyr Leu Asp Leu Tyr Leu
            100                 105                 110

Val His Trp Pro Val Ser Phe Thr Thr Gly Ser Glu Leu Phe Pro Leu
            115                 120                 125

Val Lys Asp Ser Ser Val Glu Gly Gly Asp Val Ile Asn Asp Asp
        130                 135                 140

Ile Ser Ile Val Asp Thr Trp Lys Ala Met Thr Gln Leu Pro Lys Ser
145                 150                 155                 160

Lys Ala Arg Thr Val Gly Val Ser Asn His Met Ile Pro His Leu Glu
                165                 170                 175

Ala Ile Ile Asn Ala Thr Gly Val Val Pro Ala Val Asn Gln Ile Glu
            180                 185                 190

Arg His Pro Val Leu Gln Ser Asn Glu Leu Ile Glu Tyr Cys Gln Lys
        195                 200                 205

Lys Gly Ile His Val Thr Ala Tyr Ser Ala Phe Gly Asn Asn Gly Phe
            210                 215                 220

Gly Val Pro Leu Leu Val Thr Arg Pro Glu Val Lys Glu Val Ala Glu
225                 230                 235                 240

Ser Ala Ser Lys Arg Leu Gly Thr Thr Val Thr Pro Ala Gln Val Ile
                245                 250                 255

Leu Ala Trp Ser Gln Val Gly Gly His Ser Val Ile Pro Lys Ser Val
            260                 265                 270

Thr Pro Ser Arg Ile His Glu Asn Phe Lys Glu Val Leu Thr Pro
        275                 280                 285

Glu Glu Ile Ala Lys Val Ser Glu Leu Gly Lys Asp Arg Arg Arg Tyr
290                 295                 300

Asn Thr Pro Tyr Val Ala Asn Thr Pro Arg Trp Asp Ile Asp Ile Phe
305                 310                 315                 320

Gly Glu Glu Glu Glu Lys Pro Ala Gly His Lys Val Ile Val
                325                 330

<210> SEQ ID NO 15
<211> LENGTH: 1011
<212> TYPE: DNA
<213> ORGANISM: Penicillium chrysogenum

<400> SEQUENCE: 15
atgtctctcg aaagaaagt cactctcaac accggccacc agatccccca gctgggcttt      60
ggtacctggc agtctgcccc tggccaggtc ggcgaggctg tctatgaggc cctgaaggct     120
ggttaccgcc acctggattt gcaactatc taccagaacc agcgcgaggt cgctgagggc     180
atcaagcgtg cttataagga tgtccccggt ctgaagcgcg aggatctctt tattacctcc     240
aagttgtgga acagccagca ccgccccgag gttgtcgagg cctccttgga tgcttgcctt     300
gctgagctcg agttggatta tcttgacctt taccttgttc actggcccgt tgccttccag     360
aagggcgatt catacttccc gcttgttgcc aacagccccg tcgagggtgg tgacgtgatc     420
attgacgatg cgtctccat cgtggacacc tggaaggcca tgacccagct ccccaagaac     480
aaggctcgct ccgtcggtgt ctccaaccac aagattgagc atctcgaggc tctcattaaa     540
```

```
ggcaccggtg tcgtccctgc cgccaaccag attgagcgcc accccgtgct ccagagcaac    600
gacctgattg agtactgcca acagaaggga attcacgtta ctgcttactc cgcatttggt    660
aacaacatgc tcggcattcc tctgctcatc acccgccccg aggtcaagga agttgccgag    720
tctgttgcca agcgcactgg ccaggaagtc agccccgcac acgtcattct cgcctggtct    780
caggtcggtg gacacagtgt catccccaag tcggtcacgc cttcgcgcat cgcgacaac     840
ttcaaggaga tcgaactcac tcccgaggag gtcgagaagg tcagcgctct gggccagaac    900
cggcagcgat acaacacacc ttacactgcc aacaagcctc gttgggacat tgatatcttc    960
ggcgagcccg aggagaagcc cgctggtcac aaggtcatcc tgagtgttta a            1011
```

<210> SEQ ID NO 16
<211> LENGTH: 336
<212> TYPE: PRT
<213> ORGANISM: Penicillium chrysogenum

<400> SEQUENCE: 16

```
Met Ser Leu Gly Lys Lys Val Thr Leu Asn Thr Gly His Gln Ile Pro
1               5                   10                  15

Gln Leu Gly Phe Gly Thr Trp Gln Ser Ala Pro Gly Gln Val Gly Glu
            20                  25                  30

Ala Val Tyr Glu Ala Leu Lys Ala Gly Tyr Arg His Leu Asp Leu Ala
        35                  40                  45

Thr Ile Tyr Gln Asn Gln Arg Glu Val Ala Glu Gly Ile Lys Arg Ala
    50                  55                  60

Tyr Lys Asp Val Pro Gly Leu Lys Arg Glu Asp Leu Phe Ile Thr Ser
65                  70                  75                  80

Lys Leu Trp Asn Ser Gln His Arg Pro Glu Val Val Glu Ala Ser Leu
                85                  90                  95

Asp Ala Cys Leu Ala Glu Leu Glu Leu Asp Tyr Leu Asp Leu Tyr Leu
            100                 105                 110

Val His Trp Pro Val Ala Phe Gln Lys Gly Asp Ser Tyr Phe Pro Leu
        115                 120                 125

Val Ala Asn Ser Pro Val Glu Gly Gly Asp Val Ile Ile Asp Asp Gly
    130                 135                 140

Val Ser Ile Val Asp Thr Trp Lys Ala Met Thr Gln Leu Pro Lys Asn
145                 150                 155                 160

Lys Ala Arg Ser Val Gly Val Ser Asn His Lys Ile Glu His Leu Glu
                165                 170                 175

Ala Leu Ile Lys Gly Thr Gly Val Val Pro Ala Ala Asn Gln Ile Glu
            180                 185                 190

Arg His Pro Val Leu Gln Ser Asn Asp Leu Ile Glu Tyr Cys Gln Gln
        195                 200                 205

Lys Gly Ile His Val Thr Ala Tyr Ser Ala Phe Gly Asn Asn Met Leu
    210                 215                 220

Gly Ile Pro Leu Leu Ile Thr Arg Pro Glu Val Lys Glu Val Ala Glu
225                 230                 235                 240

Ser Val Ala Lys Arg Thr Gly Gln Glu Val Ser Pro Ala His Val Ile
                245                 250                 255

Leu Ala Trp Ser Gln Val Gly Gly His Ser Val Ile Pro Lys Ser Val
            260                 265                 270

Thr Pro Ser Arg Ile Arg Asp Asn Phe Lys Glu Ile Glu Leu Thr Pro
        275                 280                 285

Glu Glu Val Glu Lys Val Ser Ala Leu Gly Gln Asn Arg Gln Arg Tyr
```

```
                   290                 295                 300
Asn Thr Pro Tyr Thr Ala Asn Lys Pro Arg Trp Asp Ile Asp Ile Phe
305                 310                 315                 320

Gly Glu Pro Glu Glu Lys Pro Ala Gly His Lys Val Ile Leu Ser Val
                325                 330                 335
```

ERYTHRITOL PRODUCTION IN CYANOBACTERIA

CROSS REFERENCE TO RELATED APPLICATIONS

This application is a 35 U.S.C. § 371 national phase application of PCT/NL2015/050195, which was filed Mar. 27, 2015, and claims the benefit of European patent application No. 14169510, filed Mar. 27, 2014, both of which are incorporated herein by reference as if fully set forth.

FIELD OF THE INVENTION

The present invention relates to a process for producing erythritol and to a cyanobacterial cell for the production of erythritol.

BACKGROUND OF THE INVENTION

Numerous biotechnological processes make use of genetically engineered organisms in order to produce bulk or fine chemicals, proteins or antibiotics. In many cases, increased production has been obtained by improved gene expression and by optimization of growth conditions. In most processes, the initial carbon-precursor has been and still is sugar (notably glucose, but many other mono- and polysaccharides are in use) or related organic substrates: solventogenesis (including butanol and ethanol) and organic acid production (e.g. lactic-, citric- or succinic acid) always starts from glucose, which makes it inefficient as the production process uses a high energy compound as input substrate.

Standard fermentation processes require a carbon source, for which plants and algal species are employed to reduce carbon dioxide via photosynthesis (using the energy of the sun) to the level of sugars and cell material. After harvesting, these end products are converted to ethanol by yeast fermentation (in the case of crops) or converted chemically to biofuels (in the case of algae). The overall energy conservation of these methods is highly inefficient and therefore demands large surface areas. In addition, the crop processes are rather labor-intensive, are demanding with respect to water consumption and affect food stock prices with adverse consequences for food supplies. A more remotely similar process is based on the conversion of solar energy into hydrogen. Also this process suffers from a severely decreased efficiency.

U.S. Pat. No. 6,699,696 describes a process of producing ethanol by feeding carbon dioxide to a cyanobacterial cell, especially a *Synechococcus* comprising a nucleic acid molecule encoding an enzyme enabling the cell to convert pyruvate into ethanol, subjecting said cyanobacterial cell to sun energy and collecting ethanol. This system has several drawbacks among others the expression system used is temperature sensitive which demands to adapt the production system for such regulation.

WO 2009/078712 describes a process of producing ethanol, propanol, butanol, acetone, 1,3-propanediol, ethylene or D-lactate and where appropriate intermediary compounds in the pathway leading to any of these organic compounds. The process is carried out by feeding carbon dioxide to a culture of cyanobacterial cells and subjecting the culture to light, wherein the cells are capable of expressing a nucleic acid molecule under the control of a regulatory system which responds to a change in the concentration of a nutrient in the culture which confers on the cell the ability to convert a glycolytic intermediate into the above-mentioned organic compounds and/or into intermediary compounds.

Erythritol is a four-carbon polyol (sugar alcohol) that is used as a sweetener in food and pharmaceutical industries. It is a naturally occurring substance, usually as a storage compound in seaweeds and fungi. Erythritol has roughly 65% of the sweetness of sucrose and is thus an attractive non-caloric substitute.

Erythritol is commercially produced via fermentation by various industries, such as Bolak Corporation (Whasung, Kyungki-do, Korea), Cargill Food & Pharm Specialties (Blair, Nebr., USA), and Mitsubishi Chemical Corporation (Tokyo, Japan). Glucose from chemically and enzymatically hydrolyzed wheat and corn starches is used as a major carbon source to produce erythritol by the fermentation of yeast-like fungi such as *Torula* sp. and *Moniliella pollinis* (Moon et al., 2010).

However, there is still a need for an improved production process of erythritol, preferably without the need of expensive or complicated starting materials, such as sugar, and which process does not have the drawbacks of existing processes such as those described here above.

DESCRIPTION OF THE INVENTION

Surprisingly, it has now been demonstrated that erythritol can conveniently be produced in a cyanobacterial cell. In brief, the inventors of the present invention have arrived at a scalable process for the production of the specific polyol, erythritol. The invention combines metabolic properties of photoautotrophic and chemoorganotrophic microorganisms and is based on the employment of recombinant oxyphototrophs with high rates of conversion of Calvin cycle intermediates to a fermentative end product. Its novelty resides in the fact that its core chemical reactions use carbon dioxide as the sole carbon-containing precursor and light (preferably sunlight), as the sole energy source, to drive carbon dioxide reduction. Moreover, the cyanobacterial cell factory is more suitable for production of erythritol than other microorganism used in fermentation processes such as *E. coli* and yeasts, since the abundantly available co-factor in the cyanobacterial cell is NADPH, rather than NADH in most chemotrophic organisms used for fermentation. Production may be controlled by a nutrient- or light-sensitive promoter. Using a nutrient-sensitive promoter, production is controlled by a medium component and can start at the most appropriate time, such as at the highest possible cell density. A light-mediated promoter is controlled by light intensity. Whereas in current production processes for biochemicals, organisms are substrate (e.g., crops in ethanol production) or product (e.g., microalgae as biodiesel), here microorganisms are used as highly specialized catalysts for the conversion of carbon dioxide as a substrate to a valuable end product. These catalysts can be subjected to further optimization strategies through physical- and chemical systems-biology approaches. The biochemical background of cyanobacterial cells for the production of valuable compounds is more extensively described in WO 2009/078712, especially in example 1. The various aspects of the present invention are more extensively described below.

In a first aspect, the present invention relates to a cyanobacterial cell capable of expressing, preferably expressing, at least one functional enzyme selected from the group of enzymes consisting of a phosphatase and a reductase. Said cyanobacterial cell is herein further referred to as a cyanobacterial cell according to the present invention. The cyanobacterial cell according to the present invention is preferably capable of producing erythritol, more preferably producing erythritol.

The term "functional enzyme" is herein preferably defined in the context of a phosphatase as an enzyme from the group of Haloacid Dehalogenase-like phosphatases, with affinity for erythrose-4-phosphate and/or erythritol-4-phosphate, such as with a Km for erythrose-4-phosphate in the range of 0.001 to 50.0 mM, more preferably 0.001 to 10mM, even more preferably 0.001 to 1mM, even more preferably 0.001 to 0.1mM, even more preferably 0.001 to 0.01mM, even more preferably 0.001 to 0.005mM.

The term "functional enzyme" is herein preferably defined in the context of a reductase as an enzyme closely related to the family of aldose reductases and able catalyze the reduction of aldehydes and preferably able to reduce either erythrose into erythritol or, erythrose-4-phosphate into erythritol-4-phosphate.

A preferred cyanobacterial cell according to the invention is capable of expressing, preferably expressing, at least one functional enzyme selected from the group consisting of enzymes having activity of an erythrose-phosphatase, an erythritol-phosphatase and an erythrose reductase; more preferably of an erythrose-4-phosphate reductase and an erythritol-4-phosphate phosphatase, or of an erythrose-4-phosphate phosphatase and an erythrose reductase. The enzyme may be native or may be heterologous to the cyanobacterial cell.

In a cyanobacterial cell according to the present invention, the at least one functional enzyme is preferably selected from the group consisting of an erythrose-4-phosphate phosphatase from *Thermotoga maritima, Escherichia coli* or *Synechocystis* PCC6803 and an erythrose-4-phosphate reductase or erythrose reductase from *Saccharomyces cerevisiae, Candida magnoliae, Trichoderma reesei, Aspergillus niger* or *Penicillium chrysogenum*.

In a cyanobacterial cell according to the present invention, the at least one functional enzyme preferably comprises or consists of a polypeptide that has an amino acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14 and SEQ ID NO: 16.

In a cyanobacterial cell according to the present invention, the at least one functional enzyme is preferably encoded by a polynucleotide that has an nucleic acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13 and SEQ ID NO: 15.

In a cyanobacterial cell according to the present invention, the at least one functional enzyme preferably is pair of enzymes consisting of a phosphatase that has an amino acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 2, SEQ ID NO: 4 and SEQ ID NO: 6; and a reductase that has an amino acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 8, SEQ ID NO: 10, SEQ ID NO: 12, SEQ ID NO: 14 and SEQ ID NO: 16.

Preferred pairs of a phosphatases and a reductase are a pair selected from the group consisting of SEQ ID NO: 2 and SEQ ID NO: 8, SEQ ID NO: 2 and SEQ ID NO: 10; SEQ ID NO: 2 and SEQ ID NO: 12, SEQ ID NO: 2 and SEQ ID NO: 14, SEQ ID NO: 2 and SEQ ID NO: 16, SEQ ID NO: 4 and SEQ ID NO: 8, SEQ ID NO: 4 and SEQ ID NO: 10, SEQ ID NO: 4 and SEQ ID NO: 12, SEQ ID NO: 4 and SEQ ID NO: 14, SEQ ID NO: 4 and SEQ ID NO: 16, SEQ ID NO: 6 and SEQ ID NO: 8, SEQ ID NO: 6 and SEQ ID NO: 10, SEQ ID NO: 6 and SEQ ID NO: 12, SEQ ID NO: 6 and SEQ ID NO: 14, and SEQ ID NO: 6 and SEQ ID NO: 16; as well as a variants of these sequences with a sequence identity of at least 30%, 35%, 40%, 45%, 50%, 55%, 60%, 65%, 70%, 75%, 80%, 90%, 91%, 92%, 93%, 94%, 95%, 96%, 97%, 98%, 99% or 100% to the respective sequence.

In a cyanobacterial cell according to the present invention, the at least one functional enzyme preferably is pair of enzymes consisting of a phosphatase encoded by a polynucleotide that has an nucleic acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 1, SEQ ID NO: 3 and SEQ ID NO: 5; and a reductase encoded by a polynucleotide that has an nucleic acid sequence with at least 30%, 35%, 40%, 45%, 50%, 55%, 60%, 65%, 70%, 75%, 80%, 90%, 91%, 92%, 93%, 94%, 95%, 96%, 97%, 98%, 99% or 100% sequence identity with a sequence selected from the group consisting of SEQ ID NO: 7, SEQ ID NO: 9, SEQ ID NO: 11, SEQ ID NO: 13 and SEQ ID NO: 15. Preferred pairs of a phosphatases and a reductase are a pair encoded by a pair of sequences selected from the group consisting of SEQ ID NO: 1 and SEQ ID NO: 7, SEQ ID NO: 1 and SEQ ID NO: 9; SEQ ID NO: 1 and SEQ ID NO: 11, SEQ ID NO: 1 and SEQ ID NO: 13, SEQ ID NO: 1 and SEQ ID NO: 15, SEQ ID NO: 3 and SEQ ID NO: 7, SEQ ID NO: 3 and SEQ ID NO: 9, SEQ ID NO: 3 and SEQ ID NO: 11, SEQ ID NO: 3 and SEQ ID NO: 13, SEQ ID NO: 3 and SEQ ID NO: 15, SEQ ID NO: 5 and SEQ ID NO: 7, SEQ ID NO: 5 and SEQ ID NO: 9, SEQ ID NO: 5 and SEQ ID NO: 11, SEQ ID NO: 5 and SEQ ID NO: 13, and SEQ ID NO: 5 and SEQ ID NO: 15; as well as a variants of these sequences with a sequence identity of at least 30%, 35%, 40%, 45%, 50%, 55%, 60%, 65%, 70%, 75%, 80%, 90%, 91%, 92%, 93%, 94%, 95%, 96%, 97%, 98%, 99% or 100% to the respective sequence.

In the context of all embodiments of the present invention, the terms "a cyanobacterium", "a cyanobacterium cell" and "a cyanobacterial cell" are used interchangeably and refer to a blue-green algae, a photosynthetic unicellular microorganism. Examples of cyanobacteria include the genera *Aphanocapsa, Anabaena, Nostoc, Oscillatoria, Synechococcus, Synechocystis, Gloeocapsa, Agmenellum, Scytonema, Mastigocladus, Arthrosprira, Haplosiphon*. A preferred order of cyanobacteria is Chroococcales. A more preferred *cyanobacterium* genus is *Synechocystis*. A more preferred species of this genus is a *Synechocystis* PCC6803 species. Even more preferably, the *Synechocystis* is a Pasteur Culture Collection (PCC) 6803 *Synechocystis*, which is a publicly available strain via ATCC for example. PCC 6803 has been stored at ATCC under ATCC27184. The phototrophic *Synechocystis* PCC 6803 is a fast growing *cyanobacterium* with no specific nutritional demands. Its physiological traits are well-documented: it is able to survive and grow in a wide range of conditions. For example, *Synechocystis* sp. PCC 6803 can grow in the absence of photosynthesis if a suitable fixed-carbon source such as glucose is provided. Perhaps most significantly, *Synechocystis* sp. PCC 6803 was the first photosynthetic organism for which the entire genome sequence was determined (available via the internet world wide web at kazusa.or.jp/cyano/cyano). In addition, an efficient gene deletion strategy (Shestakov S V et al., 2002; and Nakamura Y et al., 1999) is available for *Synechocystis* sp. PCC 6803, and this organism is furthermore easily transformable via homologous recombination (Grigirieva G A et al., 1982).

"Capable of producing erythritol" preferably means herein that detectable amounts of erythritol can be detected in a culture of a cyanobacterial cell according to the present invention cultured, under conditions conducive to the production of erythritol, preferably in the presence of light and dissolved carbon dioxide and/or bicarbonate ions, during at least 1 day using a suitable assay for detecting erythritol. A preferred concentration of said dissolved carbon dioxide and/or bicarbonate ions is, the natural occurring concentration at neutral to alkaline conditions (pH 7 to 9) being approximately 1 mM. This is equivalent to 0.035% of carbon dioxide in ambient air. A more preferred concentration of carbon dioxide and/or bicarbonate ions is higher than this natural occurring concentration. Preferably, the concentration of bicarbonate ions is at least 0.5 mM, 0.6 mM, 0.7 mM, 0.8 mM, 0.9 mM, 1 mM, 2 mM, 5 mM, 10 mM, 15 mM, 20 mM, 25 mM, 30 mM, 35 mM, 40 mM, 45 mM, 50 mM, 60 mM, 70 mM, 80 mM, 90 mM or 100 mM. A preferred method to increase the carbon dioxide and/or bicarbonate ions in solution is by enrichment with carbon dioxide, preferably waste carbon dioxide from industrial plants, sparged into the culture broth. The concentration of carbon dioxide is preferably increased to at least 0.04%, 0.05%, 0.1%, 0.15%, 0.2%, 0.5%, 1%, 1.5%, 2%, 2.5%, 3%, 3.5%, 4%, 4.5%, or 5%.

Preferably, erythritol is thus detected in a cyanobacterial cell according to the present invention and/or in its culture broth, wherein said cyanobacterial cell is cultured under conditions conducive to the production of erythritol, preferably the conditions include culturing in the presence of sunlight and carbon dioxide during at least 1 day using a given assay for the intermediary compound.

The erythritol produced within the cyanobacterial cell according to the invention may spontaneously diffuse into the culture broth. Assays for the detection of erythritol are, but not limited to, High Performance Liquid Chromatography (HPLC), Gas Chromatography (GC), Gas Chromatography-Mass Spectrometry (GC-MS), or Liquid Chromatography-Mass Spectrometry (LC-MS). A preferred assay for the detection of erythritol is High Performance Liquid Chromatography (HPLC). A detectable amount for erythritol is preferably at least 0.05 mM under said culture conditions and using said assay. Preferably, a detectable amount is at least 0.1 mM, 0.2 mM, 0.3 mM, 0.4 mM, 0.5 mM, 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, or at least 100 mM.

Preferably, a cyanobacterial cell according to the present invention comprises at least one nucleic acid molecule comprising or consisting of a polynucleotide encoding at least one of the at least one functional enzyme as defined here above. Accordingly, a preferred cyanobacterial cell according to the invention comprises at least one nucleic acid molecule comprising or consisting of a polynucleotide encoding at least one of the at least one functional enzyme as defined here above.

The at least one functional enzyme as defined here above is encoded by a polynucleotide. In all embodiments according to the invention, each encoding polynucleotide may be present on a separate nucleic acid molecule. Alternatively, the encoding polynucleotides may be present on a single nucleic acid molecule.

A preferred cyanobacterial cell according to the invention is a cyanobacterial cell wherein the at least one functional enzyme is encoded by a nucleic acid molecule comprising or consisting of a polynucleotide wherein said nucleic acid molecule is preferably present in the cyanobacterial cell as an episomal entity, preferably said episomal entity is a plasmid, more preferably a self-replicating plasmid. The episomal entity and plasmid can be any episomal entity and plasmid known to the person skilled in the art or can be based on any episomal entity and plasmid known to the person skilled in the art and modified to comprise any nucleic acid and/or polynucleotide described herein.

Another preferred cyanobacterial cell according to the invention is a cyanobacterial cell wherein the at least one functional enzyme is encoded by a nucleic acid molecule comprising or consisting of a polynucleotide wherein said nucleic acid molecule is preferably integrated in the cyanobacterial genome, preferably via homologous recombination.

A cyanobacterial cell according to the present invention may comprise a single but preferably comprises multiple copies of each nucleic acid molecule.

A preferred cyanobacterial cell according to the present invention is a cyanobacterial cell, wherein a polynucleotide encoding the at least one functional enzyme is under control of a regulatory system which responds to a change in the concentration of a nutrient when culturing said cyanobacterial cell.

A promoter that may be used for the expression of a polynucleotide encoding the at least one functional enzyme may be foreign to the polynucleotide, i.e. a promoter that is heterologous to the polynucleotide encoding the at least one functional enzyme to which it is operably linked. Although a promoter preferably is heterologous to the polynucleotide to which it is operably linked, it is also possible that a promoter is native to the cyanobacterial cell according to the present invention. Preferably, a heterologous (to the nucleotide sequence) promoter is capable of producing a higher steady state level of a transcript comprising a coding sequence (or is capable of producing more transcript molecules, i.e. mRNA molecules, per unit of time) than is a promoter that is native to the coding sequence. A suitable promoter in this context includes both a constitutive and an inducible natural promoter as well as an engineered promoter. A promoter used in a cyanobacterial cell according to the present invention may be modified, if desired, to affect its control characteristics. A preferred promoter for constitutive expression is a Ptrc, as is further outlined below in the next paragraph. The Ptrc promoter is an artificial promoter, which is constructed as a chimera of the *E. coli* trp operon and lacUV5 promoters (Brosius et al, J Biol Chem 1985). The promoter is thus regulated by the Lac repressor, LacI. In *Synechocystis*, the LacI regulated repression and induction does not function efficiently, but the Ptrc promoter does show high constitutive expression levels in the absence of LacI (Huang H-H, Camsund D, Lindblad P, Heidorn T: Design and characterization of molecular tools for a Synthetic Biology approach towards developing cyanobacterial biotechnology. Nucleic Acids Res 2010, 38:2577-2593). It was The cyanobacterial cell according to the present invention can conveniently be used for the production of erythritol.

Accordingly, in a second aspect, the present invention relates to a process for producing erythritol comprising culturing a cyanobacterial cell according to the present invention, preferably a cyanobacterial cell as defined in the first aspect of the present invention, under conditions conducive to the production of erythritol and, optionally, isolating and/or purifying the erythritol from the culture broth.

Usually a process is started with a culture (also named culture broth) of cyanobacterial cells having an optical density measured at 730 nm of approximately 0.2 to 2.0 (OD730=0.2 to 2) as measured in any conventional spectrophotometer with a measuring path length of 1 cm. Usually the cell number in the culture doubles every 20 hours. A preferred process takes place in a tank with a depth of 30-50 cm exposed to sun light. In a preferred process, the number of cells increases until the source of ammonium is exhausted or below a given value as earlier explained herein, subsequently the production of erythritol will start. Preferably, the light used is natural.

A preferred natural light is sunlight. Daylight (or sunlight) may have an intensity ranged between approximately 500 and approximately 1500 μEinstein/m 2/s. In another preferred embodiment, the light used is artificial. Such artificial light may have an intensity ranged between approximately 70 and approximately 800 μEinstein/m 2/s.

Preferably, the cells are continuously under the light conditions as specified herein. However, the cells may also be exposed to high light intensities (such as e.g. daylight/sunlight) as defined elsewhere herein for a certain amount of time, after which the cells are exposed to a lower light intensity as defined elsewhere herein for a certain amount of time, and optionally this cycle is repeated. In a preferred embodiment, the cycle is the day/night cycle.

In a preferred process, erythritol is separated from the culture broth. This may be realized continuously with the production process or subsequently to it. Separation may be based on any separation method known to the person skilled in the art.

Definitions

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

Polynucleotides described herein may be native or may be codon optimized. Codon optimization adapts the codon usage for an encoded polypeptide towards the codon bias of the organism where the polypeptide is to be produced in. Codon optimization generally helps to increase the production level of the encoded polypeptide in the host cell, such as in the preferred host herein: *Cyanobacterium Synechocystis*. Many algorithms are available to the person skilled in the art for codon optimization. A preferred method is the "guided random method based on a Monte Carlo alogorithm available via the internet world wide web genomes.urv.es/OPTIMIZER/ (P. Puigbò, E. Guzmán, A. Romeu, and S. Garcia-Vallve. Nucleic Acids Res. 2007 July; 35(Web Server issue): W126-W131).

A nucleotide sequence encoding an enzyme expressed or to be expressed in a cyanobacterial cell according to the invention or a promoter used in a cell according to the invention may be defined by its capability to hybridize with a nucleotide sequence such as SEQ ID NO: 1, 3, 5, 7, 9, 11 or 13, respectively, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

As used herein the term "heterologous sequence" or "heterologous nucleic acid" is one that is not naturally found operably linked as neighboring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

As used herein, the term "promoter" refers to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

For expression of an enzyme in a cyanobacterial cell according to the inventions, as well as for additional genetic modification of a cyanobacterial cell according to the invention, the cell can be transformed with a nucleic acid or nucleic acid construct described herein by any method known to the person skilled in the art. Such methods are e.g. known from standard handbooks, such as Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of cyanobacterial cells are known from e.g. U.S. Pat. Nos. 6,699,696 or 4,778,759.

When a nucleic acid construct is used for expression of an enzyme in a cyanobacterial cell according to the invention, a selectable marker may be present in the nucleic acid construct comprising a polynucleotide encoding the enzyme. The term "marker" refers herein to a gene encoding a trait or a phenotype which permits the selection of, or the screening for, a cyanobacterial cell containing the marker. A marker gene may be an antibiotic resistance gene whereby the appropriate antibiotic can be used to select for transformed cells from among cells that are not transformed. Preferably however, a non-antibiotic resistance marker is used, such as an auxotrophic marker (URA3, TRP1, LEU2). A preferred cyanobacterial cell according to the invention, e.g. transformed with a nucleic acid construct, is marker gene free. Methods for constructing recombinant marker gene free microbial host cells are described in (Cheah et al., 2013) and are based on the use of bidirectional markers. Alternatively, a screenable marker such as Green Fluorescent Protein, lacZ, luciferase, chloramphenicol acetyltransferase, beta-glucuronidase may be incorporated into a nucleic acid construct according to the invention allowing to screen for transformed cells.

Optional further elements that may be present in a nucleic acid construct according to the invention include, but are not limited to, one or more leader sequences, enhancers, integration factors, and/or reporter genes, intron sequences, centromers, telomers and/or matrix attachment (MAR) sequences. A nucleic acid construct according to the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual ($3^{rd}$ edition), Cold Spring Harbor Laboratory, Cold Spring Harbor Laboratory Press.

Methods for inactivation and gene disruption in a cyanobacterial cell are well known in the art (see e.g. Shestakov S V et al, (2002), Photosynthesis Research, 73: 279-284 and Nakamura Y et al, (1999), Nucleic Acids Res. 27:66-68).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the enzymes obtainable by expression of the genes as represented by SEQ ID NO's 1, 3, 5, 7, 9, 11, 13 and 15 containing the enzyme encoding polynucleotide sequences should prevail.

All patent and literature references cited in the present specification are hereby incorporated by reference in their entirety.

TABLE 1

Sequences

| SEQ ID NO | Gene/ Polypeptide | Sequence |
|---|---|---|
| 1 | phosphatase from E. coli | ATGGCTATTAAACTCATTGCTATCGATATGGATGGCACC CTTCTGCTGCCCGATCACACCATTTCACCCGCCGTTA AAAATGCGATTGCCGCAGCTCGCGCCCGTGGCGTGAA TGTCGTGCTAACGACGGGTCGCCCGTATGCAGGTGTG CACAACTACCTGAAAGAGCTGCATATGGAACAGCCGG GCGACTACTGCATTACTTATAACGGCGCGCTGGTACA GAAGGCCGCTGATGGTAGCACCGTGGCGCAAACTGCT CTCAGCTATGACGACTATCGTTTCCTGGAAAAACTCTC TCGCGAAGTCGGTTCTCATTTCCACGCCCTGGACCGCA CCACGCTGTACACCGCCAACCGTGATATCAGCTACTA CACGGTGCATGAATCCTTCGTTGCCACCATTCCGCTGG TGTTCTGCGAAGCGGAGAAAATGGACCCCAATACCCA GTTCCTGAAAGTGATGATTGATGAACCCGCCATC CTCGACCAGGCTATCGCGCGTATTCCGCAGGAAGTGA AAGAGAAATATACCGTGCTGAAAAGTGCGCCGTACTT CCTCGAAATCCTCGATAAACGCGTTAACAAAGGTACG GGGGTGAAATCACTGGCCGACGTGTTAGGTATTAAAC CGGAAGAAATCATGGCGATTGGCGATCAGGAAAACG ATATCGCAATGATTGAATATGCAGGCGTCGGTGTGGC GATGGATAACGCTATTCCTTCAGTGAAAGAAGTGGCG AACTTTGTCACCAAATCTAACCTTGAAGATGGCGTGG CGTTTGCTATTGAGAAGTATGTGCTGAATTAA |
| 2 | phosphatase from E. coli | MAIKLIAIDMDGTLLLPDHTISPAVKNAIAAARARGVNV VLTTGRPYAGVHNYLKELHMEQPGDYCITYNGALVQKA ADGSTVAQTALSYDDYRFLEKLSREVGSHFHALDRTTLY TANRDISYYTVHESFVATIPLVFCEAEKMDPNTQFLKVM MIDEPAILDQAIARIPQEVKEKYTVLKSAPYFLEILDKRV NKGTGVKSLADVLGIKPEEIMAIGDQENDIAMIEYAGVG VAMDNAIPSVKEVANFVTKSNLEDGVAFAIEKYVLN |
| 3 | phosphatase from Synechocystis sp. PCC 6803 | GTGTCAATCAAGTTAGTAGTATTGGACATTGATGGCA CCATCGCCGGAGTATCCAATCAAATTAACCCGTCAGT GGTGAAAACCATTCACCAGGTACAGAGCCGGGGTATC CAAGTGGCGTTGGCCACTGGCCGTATGTTTAGTTCTGC TCTACGGTTCCATCAGACCATTCAATCAACCCTGCCTT TGATTAGTTACAACGGTGCCCTAACCAAGCATCCCCA CACTGGTGCTGTTTTAAGGGAAAAACCCCTGCCCCCG GCGATCGCCTTGGAAATTTTGGACCATTTTGAGCGACC GGAACTGGAACCCCATCTTGATATCCACTGCTATTACA ACGACCAGCTCCATGTGCGGCATATCACCCCAGAAAC |

TABLE 1-continued

Sequences

| SEQ ID NO | Gene/Polypeptide | Sequence |
|---|---|---|
|  |  | CCATGTTTATATGGAAAGGTCCGGTGCCATGGCCCAA<br>GCTAGCGGCGATCTACGCTCAATTATTGAATTGGGTA<br>GCACCACCAAAATGTTAGCCATCAGTCGCAATGCTCC<br>CCTCATGGCCCAGTTGATGGCGGAAATGGGTCAAAAA<br>CTCCAGGGCCAAGCCGTGCATCTGACCCAATCCACCG<br>AGATTTACTTTGAAGTCACCCACGCCGAAGCCACCAA<br>AGGCCTGGCCCTGCAACATTTAGCTGAAGACGTGTTA<br>GGGCTTGATCCCCAAGAAGTTTTGGCGATCGGAGACA<br>ATTTTAACGACGTGGAAATGCTGAAATATGCCGGAGT<br>GGGGGTAGCCATGGGTAATGCTCCCCCGGAAGTGCAA<br>AAGGTGGCAGACTGGGTAACGGCGGACGTGGAAGCC<br>GATGGAGTGTCCCAAGCCTTGGCTAGGTTCTGCCTAG<br>ATTCAACCCTAGCACTCTGTTAA |
| 4 | phosphatase from *Synechocystis* sp. PCC 6803 | MSIKLVVLDIDGTIAGVSNQINPSVVKTIHQVQSRGIQVA<br>LATGRMFSSALRFHQTIQSTLPLISYNGALTKHPHTGAVL<br>REKPLPPAIALEILDHFERPELEPHLDIHCYYNDQLHVRHI<br>TPETHVYMERSGAMAQASGDLRSIIELGSTTKMLAISRN<br>APLMAQLMAEMGQKLQGQAVHLTQSTEIYFEVTHAEAT<br>KGLALQHLAEDVLGLDPQEVLAIGDNFNDVEMLKYAGV<br>GVAMGNAPPEVQKVADWVTADVEADGVSQALARFCLD<br>STLALC |
| 5 | phosphatase from *Thermotoga maritima* MSB8 | ATGGAAGCGGTGATTTTCGACATGGATGGAGTGCTCA<br>TGGACACAGAGCCTCTCTACTTCGAAGCTTACAGAAG<br>AGTCGCGGAAAGCTATGGAAAACCTTACACGGAGGAT<br>CTCCACAGGAGAATAATGGGAGTTCCTGAAAGAGAAG<br>GTCTTCCCATCCTCATGGAAGCTCTGGAGATAAAAGA<br>TTCTCTGGAGAACTTCAAAAAGAGGGTCCACGAAGAA<br>AAAAAGCGCGTTTTCTCTGAGCTTCTCAAGGAAAATC<br>CGGGTGTAAGAGAGGCGCTCGAGTTCGTAAAGAGCAA<br>AAGAATAAAACTCGCGCTCGCAACCTCCACACCACAG<br>CGAGAAGCGCTGGAGAGATTGAGAAGACTCGATCTCG<br>AAAAGTACTTCGACGTCATGGTGTTCGGTGATCAGGT<br>GAAGAACGGAAAGCCTGATCCAGAGATATACCTTCTC<br>GTTCTGGAAAGGTTGAATGTGGTCCCAGAGAAGGTTG<br>TGGTCTTCGAAGACTCAAAGAGCGGTGTTGAAGCCGC<br>AAAAAGCGCCGGCATAGAAAGAATCTATGGAGTCGTT<br>CACTCTTTGAACGACGGTAAAGCGCTTCTTGAAGCGG<br>GTGCGGTTGCTCTGGTGAAACCCGAGGAAATCCTGAA<br>CGTTCTCAAAGAGGTTCTTTAA |
| 6 | phosphatase from *Thermotoga maritima* MSB8 | MEAVIFDMDGVLMDTEPLYFEAYRRVAESYGKPYTEDL<br>HRRIMGVPEREGLPILMEALEIKDSLENFKKRVHEEKKR<br>VFSELLKENPGVREALEFVKSKRIKLALATSTPQREALER<br>LRRLDLEKYFDVMVFGDQVKNGKPDPEIYLLVLERLNV<br>VPEKVVVFEDSKSGVEAAKSAGIERIYGVVHSLNDGKAL<br>LEAGAVALVKPEEILNVLKEVL |
| 7 | aldose reductase from *Saccharomyces cerevisiae* S288c | ATGCCTGCTACTTTACATGATTCTACGAAAATCCTTTC<br>TCTAAATACTGGAGCCCAAATCCCTCAAATAGGTTTA<br>GGTACGTGGCAGTCGAAAGAGAACGATGCTTATAAGG<br>CTGTTTTAACCGCTTTGAAAGATGGCTACCGACACATT<br>GATACTGCTGCTATTTACCGTAATGAAGACCAAGTCG<br>GTCAAGCCATCAAGGATTCAGGTGTTCCTCGGGAAGA<br>AATCTTTGTTACTACAAAGTTATGGTGTACACAACACC<br>ACGAACCTGAAGTAGCGCTGGATCAATCACTAAAGAG<br>GTTAGGATTGGACTACGTAGACTTATATTTGATGCATT<br>GGCCTGCCAGATTAGATCCAGCCTACATCAAAAATGA<br>AGACATCTTGAGTGTGCCAACAAAGAAGGATGGTTCT<br>CGTGCAGTGGATATCACCAATTGGAATTTCATCAAAA<br>CCTGGGAATTAATGCAGGAACTACCAAAGACTGGTAA<br>AACTAAGGCCGTTGGAGTCTCCAACTTTTCTATAAATA<br>ACCTGAAAGATCTATTAGCATCTCAAGGTAATAAGCT<br>TACGCCAGCTGCTAACCAAGTCGAAATACATCCATTA<br>CTACCTCAAGACGAATTGATTAATTTTTGTAAAAGTAA<br>AGGCATTGTGGTTGAAGCTTATTCTCCGTTAGGTAGTA<br>CCGATGCTCCACTATTGAAGGAACCGGTTATCCTTGAA<br>ATTGCGAAGAAAATAACGTTCAACCCGGACACGTTG<br>TTATTAGCTGGCACGTCCAAAGAGGTTATGTTGTCTTG<br>CCAAAATCTGTGAATCCCGATCGAATCAAAAACGAACA<br>GGAAAATATTTACTTTGTCTACTGAGGACTTTGAAGCT<br>ATCAATAACATATCGAAGGAAAAGGGCGAAAAAAGG<br>GTTGTACATCCAAATTGGTCTCCTTTCGAAGTATTCAA<br>GTAA |

TABLE 1-continued

Sequences

| SEQ ID NO | Gene/ Polypeptide | Sequence |
|---|---|---|
| 8 | aldose reductase from *Saccharomyces cerevisiae* S288c | MPATLHDSTKILSLNTGAQIPQIGLGTWQSKENDAYKAV LTALKDGYRHIDTAAIYRNEDQVGQAIKDSGVPREEIFVT TKLWCTQHHEPEVALDQSLKRLGLDYVDLYLMHWPAR LDPAYIKNEDILSVPTKKDGSRAVDITNWNFIKTWELMQ ELPKTGKTKAVGVSNFSINNLKDLLASQGNKLTPAANQV EIHPLLPQDELINFCKSKGIVVEAYSPLGSTDAPLLKEPVI LEIAKKNNVQPGHVVISWHVQRGYVVLPKSVNPDRIKT NRKIFTLSTEDFEAINNISKEKGEKRVVHPNWSPFEVFK |
| 9 | aldose reductase from *Candida magnoliae* | ATGTCTTCGACCTACACCCTTACTCGCCTGTCTGCGCC TTCAATGGTGCTCAACAGTGGCTCCCAGATCCCTGCCG TTGGCTATGGACTCTGGAAACAGCAGGGCAGCGAGGC CAAGGACTCCGTGCGCTGCGCCATCGAGTCTGGCTAC CGTCACCTTGACTGTGCAACCGCTTACCAGAACCACA AAGAGGTCGGCCAAGCTATTCGTGAGGCCGGCGTGCC TCGCGACGAACTGTGGATCACGTCCAAGGTTTGGGGC ACGCACTTCGACAACCCTGAAGAGGGACTTGACGACA TTCTCGAGGAGCTCGGTGTCGAATACCTGGACCTGCTA CTCCTCCACCTGCCAGTCGCGTTCAAGCGGAACCCGG AGGACCCGAAGCAGCTGCGCGGCCTTCCTGTGGACCA CGACATGAAGTACGCCGACGTGTGGGCGCGCATGGAG AAGCTGCCCAAGTCGAAGGTGCGGAACATTGGTGTGT CGAACCTCACGGTGAGGGCGCTGGATGAGCTTTTGCA GACGGCGAAGGTGACTCCGGCCGTGAACCAGGTCGAG ATGCACCCGAACCTGCCTCAGAAGAAGCTGCTCGACT ACTGCAAGTCGAAGGGCATTGTTGTGCAGGCATACAG CCCTCTGGCTCAGGGCCAGCACGAGAACCCAGTTGTC ACAGACATCGCCGACGACCTCGGCGTCTCGCCGGCGC AAGTCGTGCTTTCGTGGGGCGCCTTGCGCGGCACGAA CATTCTTCCCAAATCCTCGACGCCCTCGCGTATTCGCG AGAACCTCGAACTCATCCAGCTTAGCGACGACCACAT GAGGCGTATTGACGCGCTAGCAAGACGGTGA |
| 10 | aldose reductase from *Candida magnoliae* | MSSTYTLTRLSAPSMVLNSGSQIPAVGYGLWKQQGSEA KDSVRCAIESGYRHLDCATAYQNHKEVGQAIREAGVPR DELWITSKVWGTHFDNPEEGLDDILEELGVEYLDLLLLH LPVAFKRNPEDPKQLRGLPVDHDMKYADVWARMEKLP KSKVRNIGVSNLTVRALDELLQTAKVTPAVNQVEMHPN LPQKKLLDYCKSKGIVVQAYSPLAQGQHENPVVTDIAD DLGVSPAQVVLSWGALRGTNILPKSSTPSRIRENLELIQLS DDHMRRIDALARR |
| 11 | aldose reductase from *Hypocrea jecorina* | ATGTCTTCCGGAAGGACCGTCACCCTCAACACCGGCT ACAAGATCCCCCAGATCGGCTACGGCACCTGGCAGGC CGCTCCCGGCGAGGTCGGCGCTGGTGTCTTTGAGGCC CTCAAGGTTGGCTACCGCCACCTCGACCTGGCCAAGG TCTACGGCAACCAGAAGGAGGTTGGTGAGGGCATCAA GAAGGCTCTTGCTGAGGTCCCCCGGCCTGAAGCGCGAG GATATTTTCATCACCTCCAAGCTGTGGAACAACTCCCA CAAGCCCGAGGACGTCGAGCCCGCTCTCGACGACACC CTGGCCGAGCTTGGCCTCGACTACCTTGACCTCTACCT CATCCACTGGCCCGTTGCCTTTGCTCCCGGCGCCGACC TCTTCCCCAAGTCCGAGGACGGCTCCGAGGTGCAGCT CAACCAGAATGTGTCCATTGTCCAGACCTGGAAGGCC ATGACCGAGCTGCCCAAGTCCAAGGTCCGCTCCGTCG GTGTCTCCAACTTTACCATTGAGCACCTCGACGCCGTC ATCGAGGCCACCGGCGTCGTCCCCGCCGTCAACCAGA TCGAGCGCCACCCCGCCTCCCCAACCAGCCCCTGATC GACTACTGCGCCAAGAAGGGCATCATCATCACCGCCT ACTCCGCCTTTGGCAACAACACAAAGGGCCTGCCCCT GCTCGTCAGCTCCGACGAGGTCAAGGCCGTCGCCGAC AACCTGTCCAAGAAGCAGGGCAAGACCGTCACTCCCG CCCAGGTCATCCTCGCCTGGTCCCAGATTGGTGGCCAC ACCGTCATTCCCAAGTCCGTCACCAAGGCGCGCATTG CGGAGAACTTCCAGGAGGTTGAGCTGGATGACGAGGC CATTGCTGCGCTGAACAAGTTGGGCGAGAAGCCTCAG CGGTTCAACATTCCTTACACCTACAAGCCTAGGTGGA ACATTAACCTGTTCAACACCGAGGAGGAGAAGGCCGC TGCCCACACTGCTGTCATCAAGCTGTGTAA |

TABLE 1-continued

Sequences

| SEQ ID NO | Gene/ Polypeptide | Sequence |
|---|---|---|
| 12 | aldose reductase from *Hypocrea jecorina* | MSSGRTVTLNTGYKIPQIGYGTWQAAPGEVGAGVFEAL KVGYRHLDLAKVYGNQKEVGEGIKKALAEVPGLKREDI FITSKLWNNSHKPEDVEPALDDTLAELGLDYLDLYLIHW PVAFAPGADLFPKSEDGSEVQLNQNVSIVQTWKAMTELP KSKVRSVGVSNFTIEHLDAVIEATGVVPAVNQIERHPRLP NQPLIDYCAKKGIIITAYSAFGNNTKGLPLLVSSDEVKAV ADNLSKKQGKTVTPAQVILAWSQIGGHTVIPKSVTKARI AENFQEVELDDEAIAALNKLGEKPQRFNIPYTYKPRWNI NLFNTEEEKAAAHTAVIKL |
| 13 | aldose reductase from *Aspergillus niger* | ATGTCTCTCGGAAAGAAGGTTACTCTCAACTCCGGTGC TCAGATCCCCCAGCTGGGATTTGGTACCTGGCAGTCTG CCCCCGGTCAGGTCGGTGATGCCGTCTACGAGGCCTT GAAGGCCGGCTACCGCCACTTGGATCTGGCTACTATCT ACCAGAACCAGCGCGAGGTTGCTGAGGGCATCAAGAG AGCCTACAAGGACGTCCCTGGCCTCAAGCGTGAGGAC ATCTTCATCACCTCCAAGCTGTGGAACTCCCAGCACGA CCCCGCCGTTGTTGAGAAGGCTCTGGATGAGTGCCTTG CTGAGCTCGAGCTCGACTACCTCGATCTCTACCTCGTC CACTGGCCCGTTTCCTTCACCACCGGCTCCGAGTTGTT CCCCCTCGTCAAGGACAGCTCCGTTGAGGGCGGTGAT GTCGTGATCAACGACGACATCTCCATCGTCGACACCT GGAAGGCCATGACCCAGCTCCCCAAGAGCAAGGCCCG CACCGTCGGTGTCTCCAACCACATGATCCCTCACCTCG AGGCCATCATCAACGCCACCGGCGTTGTCCCCGCCGTT AACCAGATCGAGCGCCACCCCGTTCTCCAGAGCAACG AGCTCATCGAATACTGCCAGAAGAAGGGCATCCACGT GACCGCCTACTCTGCCTTCGGCAACAACGGCTTCGGC GTCCCCCTCCTCGTCACCCGCCCCGAAGTCAAGGAAG TCGCTGAGTCCGCCTCCAAGCGCCTCGGCACCACCGTC ACCCCTGCCCAGGTCATCCTGGCCTGGTCCCAGGTCGG CGGCCACAGTGTCATCCCCAAGTCGGTGACGCCGTCC CGCATCCATGAGAACTTCAAGGAGGTGGAGCTCACTC CCGAGGAAATCGCCAAGGTGTCCGAGCTGGGCAAGGA CCGCAGACGCTACAACACTCCTTACGTTGCTAACACG CCTCGCTGGGATATCGACATCTTCGGTGAGGAGGAGG AGAAGCCTGCTGGTCATAAGGTGATTGTTTAA |
| 14 | aldose reductase from *Aspergillus niger* | MSLGKKVTLNSGAQIPQLGFGTWQSAPGQVGDAVYEAL KAGYRHLDLATIYQNQREVAEGIKRAYKDVPGLKREDIF ITSKLWNSQHDPAVVEKALDECLAELELDYLDLYLVHW PVSFTTGSELFPLVKDSSVEGGDVVINDDISIVDTWKAMT QLPKSKARTVGVSNHMIPHLEAIINATGVVPAVNQIERHP VLQSNELIEYCQKKGIHVTAYSAFGNNGFGVPLLVTRPE VKEVAESASKRLGTTVTPAQVILAWSQVGGHSVIPKSVT PSRIHENFKEVELTPEEIAKVSELGKDRRRYNTPYVANTP RWDIDIFGEEEEKPAGHKVIV |
| 15 | aldose reductase from *Penicillium chrysogenum* | ATGTCTCTCGGAAAGAAAGTCACTCTCAACACCGGCC ACCAGATCCCCCAGCTGGGCTTTGGTACCTGGCAGTCT GCCCCTGGCCAGGTCGGCGAGGCTGTCTATGAGGCCC TGAAGGCTGGTTACCGCCACCTGGATTTGGCAACTATC TACCAGAACCAGCGCGAGGTCGCTGAGGGCATCAAGC GTGCTTATAAGGATGTCCCCGGTCTGAAGCGCGAGGA TCTCTTTATTACCTCCAAGTTGTGGAACAGCCAGCACC GCCCCGAGGTTGTCGAGGCCTCCTTGGATGCTTGCCTT GCTGAGCTCGAGTTGGATTATCTTGACCTTTACCTTGT TCACTGGCCCGTTGCCTTCCAGAAGGGCGATTCATACT TCCCGCTTGTTGCCAACAGCCCCGTCGAGGGTGGTGA CGTGATCATTGACGATGGCGTCTCCATCGTGGACACCT GGAAGGCCATGACCCAGCTCCCCAAGAACAAGGCTCG CTCCGTCGGTGTCTCCAACCACAAGATTGAGCATCTCG AGGCTCTCATTAAAGGCACCGGTGTCGTCCCTGCCGCC AACCAGATTGAGCGCCACCCCGTGCTCCAGAGCAACG ACCTGATTGAGTACTGCCAACAGAAGGGAATTCACGT TACTGCTTACTCCGCATTTGGTAACAACATGCTCGGCA TTCCTCTGCTCATCACCCGCCCCGAGGTCAAGGAAGTT GCCGAGTCTGTTGCCAAGCGCACTGGCCAGGAAGTCA GCCCCGCACACGTCATTCTCGCCTGGTCTCAGGTCGGT GGACACAGTGTCATCCCCAAGTCGGTCACGCCTTCGC GCATTCGCGACAACTTCAAGGAGATCGAACTCACTCC |

TABLE 1-continued

Sequences

| SEQ ID NO | Gene/ Polypeptide | Sequence |
|---|---|---|
| | | CGAGGAGGTCGAGAAGGTCAGCGCTCTGGGCCAGAAC CGGCAGCGATACAACACACCTTACACTGCCAACAAGC CTCGTTGGGACATTGATATCTTCGGCGAGCCCGAGGA GAAGCCCGCTGGTCACAAGGTCATCCTGAGTGTTTAA |
| 16 | aldose reductase from *Penicillium chrysogenum* | MSLGKKVTLNTGHQIPQLGFGTWQSAPGQVGEAVYEAL KAGYRHLDLATIYQNQREVAEGIKRAYKDVPGLKREDL FITSKLWNSQHRPEVVEASLDACLAELELDYLDLYLVH WPVAFQKGDSYFPLVANSPVEGGDVIIDDGVSIVDTWKA MTQLPKNKARSVGVSNHKIEHLEALIKGTGVVPAANQIE RHPVLQSNDLIEYCQQKGIHVTAYSAFGNNMLGIPLLITR PEVKEVAESVAKRTGQEVSPAHVILAWSQVGGHSVIPKS VTPSRIRDNFKEIELTPEEVEKVSALGQNRQRYNTPYTAN KPRWDIDIFGEPEEKPAGHKVILSV |

FIGURE LEGENDS

FIG. 1. Catabolic pathways for formation of erythritol in a *cyanobacterium* including the enzymes involved.

Figure 2:
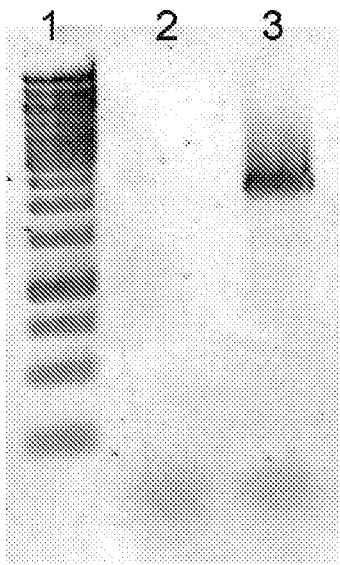

FIG. 2. Colony PCR to confirm the correct insertion of the plasmid into *Synechocystis*. Lane 1: DNA ladder; lane 2: negative control; lane 3: *Synechocystis* strain SAW030 with plasmid conferring erythritol production.

Figure 3:
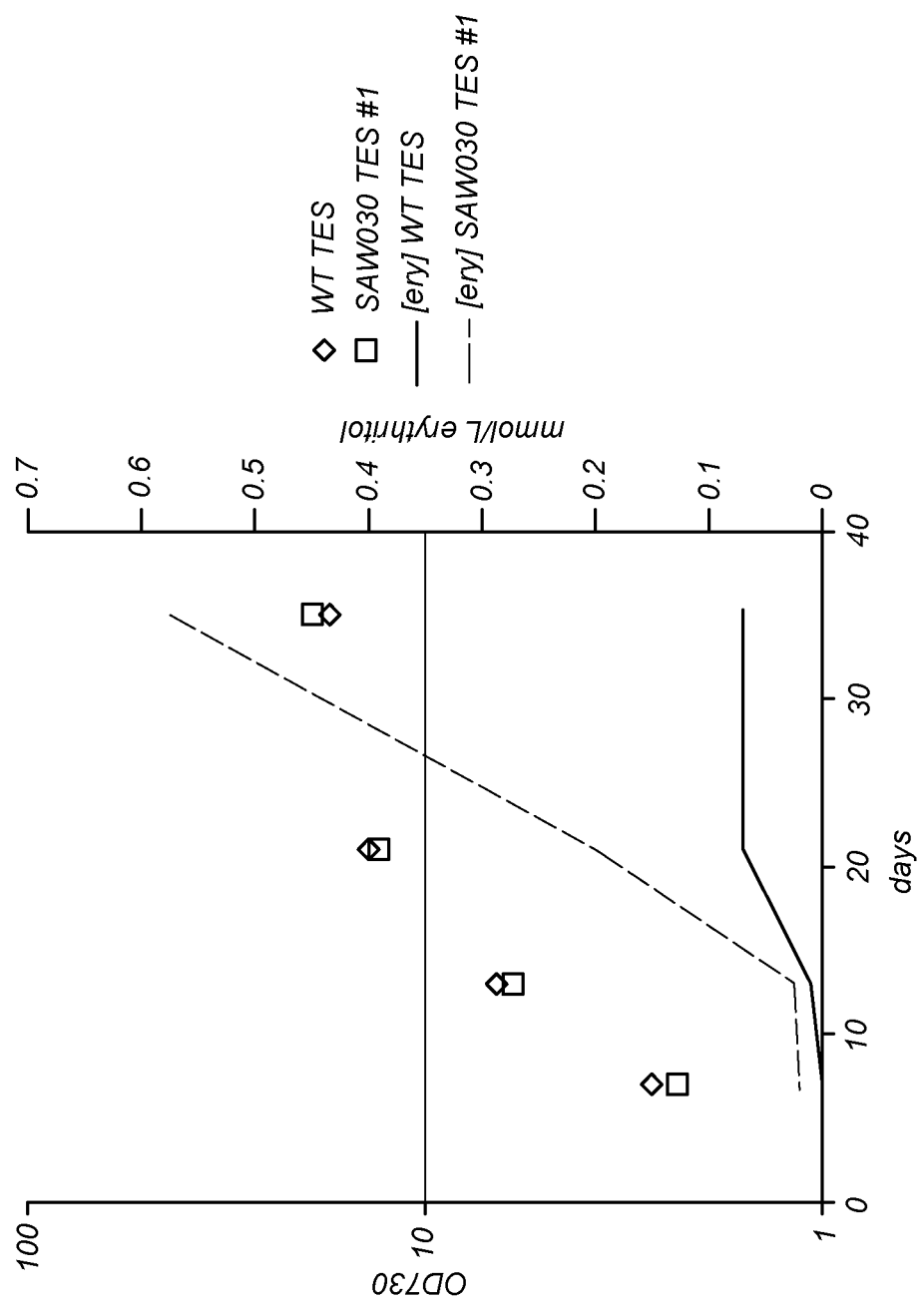

FIG. 3. Growth and level of erythritol production in the supernatant of SAW030 and wild type *Synechocystis*.

Figure 4:
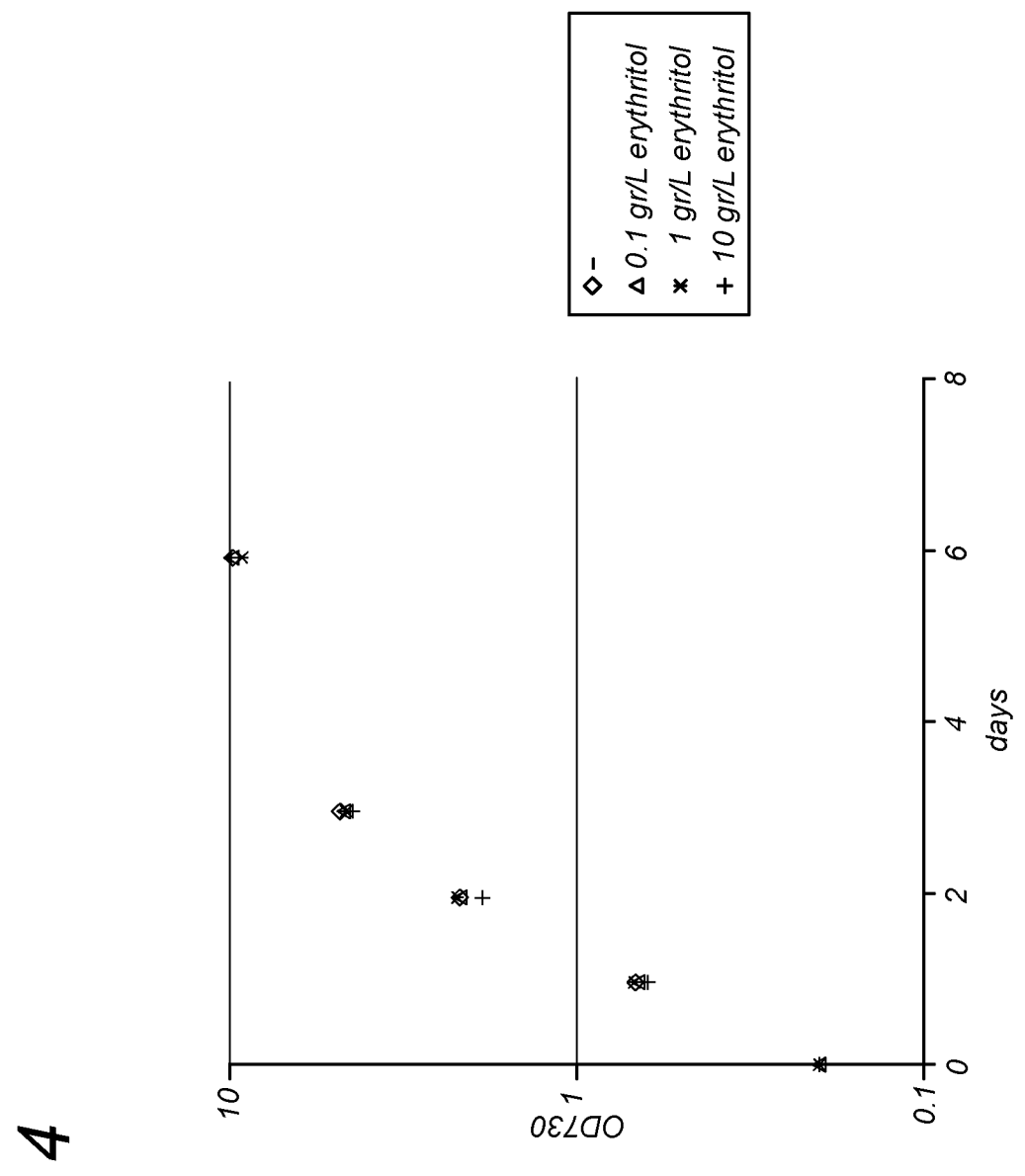

FIG. 4. Toxicity assay for erythritol.

Figure 5:
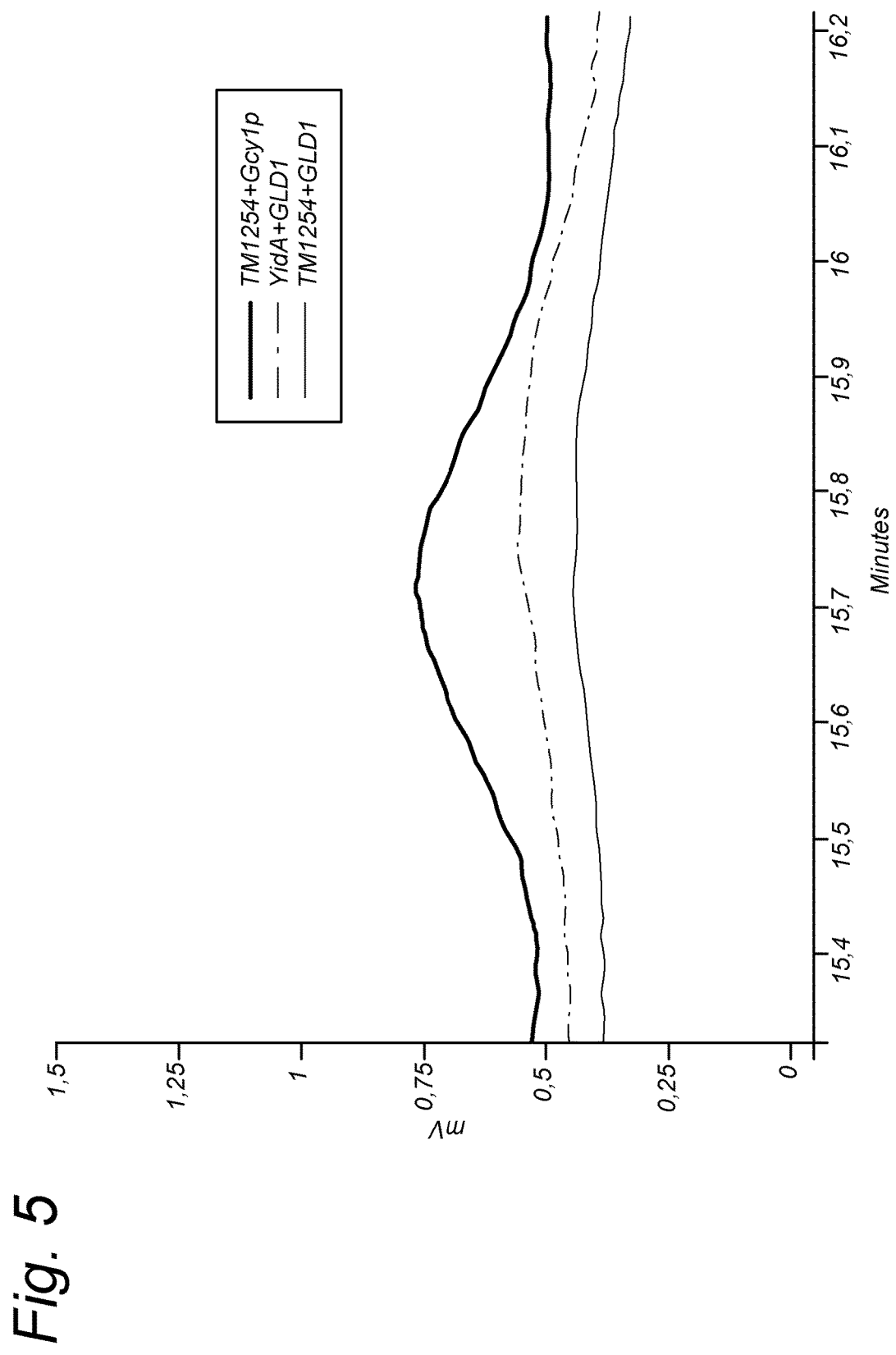

FIG. 5. HPLC data showing the level of erythritol production measured in the supernatant of different *Synechocystis* erythritol producing strains.

EXAMPLES

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

Example 1

Cloning Strategy

We have introduced a specific two enzyme catabolic pathway into a cyanobacterial cell to produce erythritol.

Two catabolic pathways for the formation of erythritol from erythrose-4-phosphate have been reported in literature (FIG. 1). The pathway of erythritol formation has been best studied in yeast, in which erythrose-4-phosphate (E4P) is first dephosphorylated to d-erythrose, and then reduced to erythritol. In bacteria, erythrose-4-phosphate is described to be reduced to erythritol-4-phosphate first, but the enzymes involved are unknown (Veiga-da-Cunha M, Santos H, Van Schaftingen E: Pathway and regulation of erythritol formation in *Leuconostoc oenos*. J Bacteriol 1993, 175:3941-3948).

Phosphatase: of the group of Haloacid Dehalogenase-like phosphatases, with affinity for erythrose-4-phosphate or erythritol-4-phosphate. Such phosphatases usually have a quite broad substrate specificity, but for example YidA (derived from *Escherichia coli*) has a quite attractive Km for erythrose-4-phosphate.

Reductase: Closely related to the family of aldose reductases and can usually catalyze the reduction of several aldehydes. Should be able to reduce either erythrose into erythritol or erythrose-4-phosphate into erythritol-4-phosphate.

TABLE 2

Characteristics of phosphatases

| gene | donor organism | D-erythrose-4-P | | Vmax (umol/min/mg protein) | SEQ ID NO: | ref |
|---|---|---|---|---|---|---|
| | | Km (mM) | Kcat (s-1) | | | |
| TM1254 | *Thermotoga maritima* MSB8 | 0.152 | — | 2.63 | 5, 6 | Kunetsova et al, 2005 |
| YidA | *Escherichia coli* | 0.019 | 19 | — | 1, 2 | Kunetsova et al, 2006 |
| sll1524 | *Synechocystis* PCC6803 | — | — | — | 3, 4 | |

TABLE 3

Characteristics of reductases

| gene | donor organism | SEQ ID NO: | D-erythrose Km (mM) | D-erythrose Kcat (s-1) | NADPH Km | NADPH Kcat (s-1) | ref |
|---|---|---|---|---|---|---|---|
| ErCm | *Candida magnolia* JH110 | 9, 10 | 8.5 | 7.6 | 0.016 | 48 | (Lee et al, 2010) |
| Gcy1p | *Saccharomyces cerevisiae* | 7, 8 | 3.4 | — | — | — | Ookura et al, 2007 |
| GLD1 | *Hypocrea jecorina* (*Trichoderma reesei*) | 11, 12 | 0.016-0.134 | 530-36.5 | — | — | Jovanović et al, 2013 |
| ALR1 | *Aspergillus niger* | 13, 14 | 0.139 | 25 | | | Jovanović et al, 2013 |
| Pc20g15580 | *Penicillium chrysogenum* | 15, 16 | ? | ? | | | |

Example 2

Biochemical Background of a Cyanobacterial Cell According to the Present Invention The genes encoding the phosphatase TM_1254, derived from *Thermotoga maritima* MSB8 (Kuznetsova et al., 2005), and the erythrose reductase Gcy1p, derived from *Saccharomyces cerevisiae* (Ookura and Kasumi, 2007) were codon-optimized for expression in *Synechocystis* and obtained through chemical synthesis. These genes were each cloned with a trc promoter into a RSF 1010-based conjugative plasmid pVZ. Introduction of the phosphatase-encoding gene, in combination with a gene encoding one of the erythrose reductases (via a conjugative plasmid) should allow the transconjugant *Synechocystis* strain to produce erythritol from erythrose-4-phosphate. These strains were tested by colony PCR to confirm the presence of the plasmid (FIG. 2). FIG. 2 depicts SAW030 in the third lane with a band of ~2200 bp, representing the phosphatase and reductase, whereas the second lane shows wildtype *Synechocystis* as a negative control.

Example 3

Production of Erythritol by a Cyanobacterial Cell

Mutant cultures obtained in example 2 were selected for presence of the plasmid by growth on agar plates containing 20 μg/ml of kanamycine. A selected mutant was named *Synechocystis* SAW030. This SAW030 mutant was inoculated in BG-11 medium supplemented with 10 mM TES-buffer-NaOH (pH=8.0) and 20 ug/ml kanamycine and grown to stationary phase within several days (OD of 1.5). An aliquot of the initial culture was used to inoculate 100 ml BG-11 supplemented with 10 mM TES-buffer-NaOH (pH=8.0) and with 10 μg/ml kanamycine to an OD of 0.1. The culture was incubated at low light intensity (~40 μE), 30° C. and shaking at 120 rpm. After every few days, an 800 μl sample was taken for measurement of optical density (A730) and determination of erythritol concentration in the supernatant. With the help of standard concentrations of erythritol, the concentration of erythritol in the culture was determined via an HPLC method (FIG. 3). In conclusion, erythritol production increases in time (at least up to 35 days) to a concentration of at least 550 uM (60 mg/L) in the extracellular medium.

Example 4

Resistance to Erythritol of *Synechocystis* PCC6803

*Synechocystis* PCC6803 was inoculated in 10 ml BG-11 supplemented with 10 mM TES-buffer-NaOH (pH=8.0) and with 10 μg/ml kanamycine at an OD of 0.2. The culture was incubated at low light intensity (~40 μE), 30° C. and shaking at 120 rpm. It was clearly shown (FIG. 4) that up to a concentration of 10 gr/L erythritol, cultures are not affected with respect to growth-rate.

Example 5

Biochemical Background and Production of Erythritol of Several Additional Cyanobacterial Cells According to the Present Invention The genes encoding phosphatases TM_1254 and YidA, and the erythrose reductases Gcy1p, GLD1, ALR1 and Pc20g15580 were codon-optimized for expression in *Synechocystis* and obtained by chemical synthesis. These genes were each cloned with a trc promoter into a vector containing homologous regions targeting for genome integration at the slr0168 gene. Introduction of the phosphatase-encoding gene, in combination with a gene encoding one of the erythrose reductases (via natural transformation and homologous recombination) allows the transformant *Synechocystis* strains to produce erythritol from erythrose-4-phosphate. Mutant cultures were selected for by growth on agar plates containing 20 μg/ml of kanamycine. The resulting strains were tested by colony PCR to confirm the presence of the desired genes in the genome. From the strains obtained, strains comprising TM1254 and GLD1, YidA and GLD1, and TM1254 and Gcy1p were selected for further analysis.

These strains were inoculated in BG-11 medium supplemented with 25 mM CAPSO-buffer-NaOH (pH=9.0) and 20 ug/ml kanamycine and grown to stationary phase within several days (OD of 1.5). An aliquot of the initial culture was used to inoculate 100 ml BG-11 supplemented with 25 mM CAPSO-buffer-NaOH (pH=9.0) and 20 ug/ml kanamycine to an OD of 0.1. The culture was incubated at low light intensity (~40 μE), 30° C. and shaking at 120 rpm. After 23-30 days of culture, an 800 μl sample was taken for measurement of optical density (A730) and for determination of erythritol concentration in the supernatant. Using standard concentrations of erythritol, the concentration of erythritol in the culture was determined using HPLC (FIG. 5). In conclusion, erythritol production was detected in the extracellular medium of each of the tested strains; strain TM1254/GLD1 produced 0.05 mM erythritol (retention 15.75 min.), strain YidA/GLD1 produced 0.09 mM erythritol (retention 15.75 min.), and strain TM1254/Gcy1p produced 0.1 mM erythritol (retention 15.72 min.). These results are clearly in the same magnitude as strain SAW030 in example 3.

REFERENCE LIST

1. Moon et al., (2010) Appl Microbiol Biotechnol 2010, 86:1017-1025.
2. Computational Molecular Biology, Lesk, A. M., ed., Oxford University Press, New York, 1988;
3. Biocomputing: Informatics and Genome Projects, Smith, D. W., ed., Academic Press, New York, 1993;
4. Computer Analysis of Sequence Data, Part I, Griffin, A. M., and Griffin, H. G., eds., Humana Press, New Jersey, 1994;
5. Sequence Analysis in Molecular Biology, von Heine, G., Academic Press, 1987;
6. Sequence Analysis Primer, Gribskov, M. and Devereux, J., eds., M Stockton Press, New York, 1991; and Carillo, H., and Lipman, D., SIAM J. Applied Math., 48:1073, 1988.
7. Devereux, J., et al., Nucleic Acids Research 12 (1): 387, 1984.
8. Altschul, S. F. et al., J. Mol. Biol. 215:403-410, 1990.
9. BLAST Manual, Altschul, S., et al., NCBI NLM NIH Bethesda, MD 20894; Altschul, S., et al., J. Mol. Biol. 215:403-410, 1990.
10. Needleman and Wunsch, J. Mol. Biol. 48:443-453, 1970.
11. Hentikoff and Hentikoff, Proc. Natl. Acad. Sci. USA. 89:10915-10919, 1992.
12. Puigbò, E. Guzman, A. Romeu, and S. Garcia-Vallve. Nucleic Acids Res. 2007 July; 35(Web Server issue): W126-W131.
13. Sambrook and Russel (2001) "Molecular Cloning: A Laboratory Manual (3$^{rd}$ edition), Cold Spring Harbor Laboratory, Cold Spring Harbor Laboratory Press.
14. Ausubel et al, eds., "Current protocols in molecular biology", Green Publishing and Wiley Interscience, New York, 1987.
15. Cheah et al, (2013) Biotechnol Prog 2013, 29:23-30.
16. Shestakov S V et al, (2002), Photosynthesis Research, 73: 279-284
17. Nakamura Y et al, (1999), Nucleic Acids Res. 27:66-68
18. Sambrook et al. (1989) Molecular Cloning, A Laboratory Manual (2$^{nd}$ edition), Cold Spring Harbor Laboratory, Cold Spring Harbor Laboratory Press
19. Volumes 1 and 2 of Ausubel et al. (1994) *Current Protocols in Molecular Biology, Current Protocols*, USA.
20. Volumes I and II of Brown (1998) *Molecular Biology LabFax*, Second Edition, Academic Press (UK).
21. Veiga-da-Cunha M, Santos H, Van Schaftingen E: Pathway and regulation of erythritol formation in *Leuconostoc oenos*. J Bacteriol 1993, 175:3941-3948.
22. Brosius et al, J Biol Chem 1985
23. Huang H-H, Camsund D, Lindblad P, Heidorn T: Design and characterization of molecular tools for a Synthetic Biology approach towards developing cyanobacterial biotechnology. *Nucleic Acids Res* 2010, 38:2577-2593.
24. Kuznetsova E, Proudfoot M, Gonzalez C F, Brown G, Omelchenko MV, Borozan I, Carmel L, Wolf Y I, Mori H, Savchenko A V, Arrowsmith C H, Koonin E V, Edwards A M, Yakunin A F: Genome-wide analysis of substrate specificities of the *Escherichia coli* haloacid dehalogenase-like phosphatase family. J Biol Chem 2006, 281: 36149-36161.
25. Kuznetsova E, Proudfoot M, Sanders S A, Reinking J, Savchenko A, Arrowsmith C H, Edwards A M, Yakunin A F: Enzyme genomics: Application of general enzymatic screens to discover new enzymes. FEMS Microbiol Rev 2005, 29:263-279
26. Jovanovie B, Mach R L, Mach-Aigner A R: Characterization of erythrose reductases from filamentous fungi. AMB Express 2013, 3:43.
27. Ookura T, Kasumi T: Yeast Gcy1p Reduces Erythrose and Erythrose-4-phosphate. Rep Natl Food Res Inst 2007, 71:57-60.
28. Lee D-H, Lee Y-J, Ryu Y-W, Seo J-H: Molecular cloning and biochemical characterization of a novel erythrose reductase from Candida magnoliae JH110. Microb Cell Factories 2010, 9:43.

The invention claimed is:

1. A cyanobacterial cell comprising a polynucleotide encoding a phosphatase that comprises an amino acid sequence with at least 90% sequence identity with SEQ ID NO: 2 and a polynucleotide encoding a reductase that comprises an amino acid sequence with at least 90% sequence identity with SEQ ID NO: 12.

2. The cyanobacterial cell according to claim 1, wherein the polynucleotide encoding the phosphatase comprises a nucleic acid sequence with at least 80% sequence identity with SEQ ID NO: 1, and wherein the polynucleotide encoding the reductase comprises a nucleic acid sequence with at least 80% sequence identity with SEQ ID NO: 11.

3. The cyanobacterial cell according to claim 1, wherein the cyanobacterial cell is a *Synechocystis* cell.

4. The cyanobacterial cell according to claim 1, wherein the polynucleotide encoding the phosphatase and/or the polynucleotide encoding the reductase is under control of a regulatory system which responds to a change in the concentration of a nutrient when culturing said cyanobacterial cell.

5. The cyanobacterial cell according to claim 3, wherein the cyanobacterial cell is a *Synechocystis* PCC 6803 cell.

6. The cyanobacterial cell according to claim 1, wherein the phosphatase comprises the amino acid sequence of SEQ ID NO: 2 and wherein the reductase comprises the amino acid sequence of SEQ ID NO: 12.

7. The cyanobacterial cell according to claim 2, wherein the polynucleotide encoding the phosphatase comprises the nucleic acid sequence of SEQ ID NO: 1 and wherein the polynucleotide encoding the reductase comprises the nucleic acid sequence of SEQ ID NO: 11.

8. A process for producing erythritol comprising culturing the cyanobacterial cell according to claim 1 under conditions conducive to the production of erythritol and, optionally, isolating and/or purifying the erythritol from the culture broth.

9. The process according to claim 8, wherein the culture conditions comprise feeding carbon dioxide to the culture and/or subjecting the culture to light.

* * * * *